US012636386B2

(12) United States Patent
Baranowska-Kortylewicz et al.

(10) Patent No.: US 12,636,386 B2
(45) Date of Patent: May 26, 2026

(54) COMPOSITIONS AND METHODS FOR THE TREATMENT AND IMAGING OF CANCER

(71) Applicant: BOARD OF REGENTS OF THE UNIVERSITY OF NEBRASKA, Lincoln, NE (US)

(72) Inventors: Janina Baranowska-Kortylewicz, Omaha, NE (US); Zbigniew Kortylewicz, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 942 days.

(21) Appl. No.: 17/689,200

(22) Filed: Mar. 8, 2022

(65) Prior Publication Data

US 2022/0280662 A1 Sep. 8, 2022

Related U.S. Application Data

(60) Provisional application No. 63/157,952, filed on Mar. 8, 2021.

(51) Int. Cl.
*A61K 51/04* (2006.01)
*A61P 35/00* (2006.01)

(52) U.S. Cl.
CPC .......... *A61K 51/0491* (2013.01); *A61P 35/00* (2018.01)

(58) Field of Classification Search
USPC ...................................... 424/1.65, 1.81-1.89
See application file for complete search history.

(56) References Cited

U.S. PATENT DOCUMENTS

| | | | |
|---|---|---|---|
| 10,874,752 | B2 | 12/2020 | Baranowska-Kortylewicz et al. |
| 2010/0104682 | A1 | 4/2010 | Ludeman et al. |
| 2013/0149244 | A1 | 6/2013 | Purohit et al. |

FOREIGN PATENT DOCUMENTS

| | | | |
|---|---|---|---|
| WO | 2009/018088 | A2 | 2/2009 |

OTHER PUBLICATIONS

Gallagher FA et al. Imaging breast cancer using hyperpolarized carbon-13 MRI. Proc Natl Acad Sci U S A. 117(4):2092-2098. (Jan. 21, 2020) (Year: 2020).*

Prat, A. et al. The role of hormonal therapy in the management of hormonal-receptor-positive breast cancer with co-expression of HER2. Nat Rev Clin Oncol 5, 531â542 (Jul. 8, 2008) (Year: 2007).*

Riethdorf, S. et al. Detection of circulating tumor cells in peripheral blood of patients with metastatic breast cancer: a validation study of the CellSearch system. Clinical cancer research, 13(3), 920-928. (Feb. 8, 2007) (Year: 2007).*

Kortylewicz Z. P. et al. Radiolabeled (R)-(-)-5-iodo-3'-O-[2-(ε-guanidinohexanoyl)-2-phenylacetyl]-20-deoxyuridine: A new theranostic for neuroblastoma. J. Label Compd. Radiopharm. 63:312-324 (2020) (Year: 2020).*

Patani G. et al. "Bioisosterism: A Rational Approach in Drug Design." Chem. Rev. 96:3147-3176 (1996) (Year: 1996).*

Kortylewicz, et al. "Norepinephrine-Transporter-Targeted and DNA-Co-Targeted Theranostic Guanidines" J. Med. Chem. (2020) 63:2051-2073.

Kortylewicz, et al. "Radiolabeled (R)-(-)-5-iodo-30-O-[2-(ε-guanidinohexanoyl)-2-phenylacetyl]-20-deoxyuridine: A new theranostic for neuroblastoma" J. Label Compd. Radiopharm. (2020) 63:312-324.

Chen, et al., "Novel "Add-On" Molecule Based on Evans Blue Confers Superior Pharmacokinetics and Transforms Drugs to Theranostic Agents" J. Nucl. Med. (2017) 58(4):590-597.

Bandara, et al., "Novel Structural Modification Based on Evans Blue Dye to Improve Pharmacokinetics of a Somastostatin-Receptor-Based Theranostic Agent" Bioconjug Chem. (2018) 29(7):2448-2454.

Kortylewicz, et al. "Radiolabeled 5-iodo-3'-O-(17beta-succinyl-5alpha-androstan-3-one)-2'-deoxyuridine and its 5'-monophosphate for imaging and therapy of androgen receptor-positive cancers: synthesis and biological evaluation" J. Med. Chem. (2009) 52(16):5124-43.

* cited by examiner

*Primary Examiner* — Michael G. Hartley

(74) *Attorney, Agent, or Firm* — Robert C. Netter, Jr.; Dann, Dorfman, Herrell & Skillman

(57) ABSTRACT

Compositions and methods for treating, detecting, and diagnosing cancer and other diseases and disorders are disclosed.

21 Claims, 8 Drawing Sheets

COMPOSITIONS AND METHODS FOR THE TREATMENT AND IMAGING OF CANCER

This application claims priority under 35 U.S.C. § 119(e) to U.S. Provisional Patent Application No. 63/157,952, filed on Mar. 8, 2021. The foregoing application is incorporated by reference herein.

FIELD OF THE INVENTION

The present invention relates to the field of therapeutics and cancer imaging agents. Specifically, the instant invention provides novel chemotherapeutic and imaging agents and methods of use thereof.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

Childhood cancers represent less than 2% of all human cancers, and yet in children 1 year or older, these malignancies are responsible for more deaths than all other diseases combined (GBD 2017 Childhood Cancer Collaborators (2019) Lancet Oncol., 20(9):1211-1225). Every day, 43 children are diagnosed with cancer. In the United States, one in five children with cancer will not survive, even after intensive multimodality treatments. Moreover, the majority of childhood cancer survivors experience late, chronic side effects that adversely affect their adult lives (Phillips, et al. (2015) Cancer Epidemiol. Biomarkers Prev., 24(4):653-663). New treatments are needed to eliminate, or at least appreciably diminish, acute toxicities, minimize long-term morbidities of current therapies, and improve cure rates for children who do not respond to existing treatments.

SUMMARY OF THE INVENTION

In accordance with the instant invention, norepinephrine transporter and DNA co-targeted compounds are provided. In certain embodiments, the compound is of Formula (I), (II), or (III), or a pharmaceutically acceptable salt or stereoisomer thereof. In certain embodiments, the X of Formula (I), (II), or (III) comprises an Auger electron-emitting radionuclide. In certain embodiments, the X of Formula (I), (II), or (III) comprises a radiohalogen. In certain embodiments, the X of Formula (I), (II), or (III) comprises selected from the group consisting of $^{123}$I, $^{124}$I, $^{125}$I, $^{131}$I, $^{211}$At, $^{18}$F, $^{76}$Br, $^{77}$Br, and $^{80m}$Br. In certain embodiments, the X of Formula (I), (II), or (III) comprises a radioactive iodine. In certain embodiments, the X of Formula (I), (II), or (III) comprises $^{123}$I, $^{124}$I, or $^{125}$I. In certain embodiments, the R of Formula (I) or (II) is an aryl. In certain embodiments, the compound is (R)-(−)-5-iodo-3'-O-[2-(ε-guanidinohexanoyl)-2-phenylacetyl]-2'-deoxyuridine (GPAID, 9).

In accordance with another aspect of the instant invention, compositions comprising a compound of the instant invention and a pharmaceutically acceptable carrier are also provided. The composition may further comprise an anti-cancer therapeutic agent.

In accordance with another aspect of the instant invention, methods of treating, inhibiting, and/or preventing a cancer in a subject are provided. In certain embodiments, the method comprises administering a compound of the instant invention or composition comprising the same to the subject. In certain embodiments, the cancer expresses the norepinephrine transporter. In certain embodiments, the cancer is neuroblastoma.

In accordance with another aspect of the instant invention, methods of treating, inhibiting, and/or preventing other norepinephrine transporter associated diseases or disorders such as an attention-deficit hyperactivity disorder, substance abuse, neurodegenerative disorder, and/or depression in a subject are provided. In certain embodiments, the method comprises administering a compound of the instant invention or composition comprising the same to the subject.

In accordance with another aspect of the instant invention, methods for imaging and/or detecting a tumor or cancerous tissue in a subject are provided. In certain embodiments, the method comprises administering a compound of the instant invention to the subject and determining the location of the radioactivity within the subject. The detection step can be performed at more than one timepoint (optionally after an additional administration of the compound) to monitor the progression of a cancer or response to a therapy in a subject. In certain embodiments, the cancer expresses the norepinephrine transporter. In certain embodiments, the cancer is neuroblastoma.

In accordance with another aspect of the instant invention, methods for imaging and/or detecting other norepinephrine transporter associated diseases or disorders such as an attention-deficit hyperactivity disorder, substance abuse, neurodegenerative disorder, and/or depression in a subject are provided. In certain embodiments, the method comprises administering a compound of the instant invention to the subject and determining the location of the radioactivity within the subject. The detection step can be performed at more than one timepoint (optionally after an additional administration of the compound) to monitor the progression of the norepinephrine transporter associated disease or disorder such as an attention-deficit hyperactivity disorder, substance abuse, neurodegenerative disorder, and/or depression or response to a therapy in a subject.

BRIEF DESCRIPTION OF THE DRAWINGS

FIG. 2A: Stability curves derived from HPLC analyses of GPAID incubated in human serum (circles) and pig serum (triangles). Solid lines are the monoexponential fit of the percent intact GPAID as a function of various times of incubation. FIG. 2B: Composition of the mixture recovered after 17-minute incubation of GPAID in mouse serum. FIG. 2C: GPAID recovered from culture medium without cells incubated for 24 hours at 37° C. and 5% $CO_2$. FIG. 2D: Radioactivity profile of medium collected from SK-N-SH cells cultured with GPAID for 24 hours at 37° C., 5% $CO_2$. * indicates that the peak contains ~30% of total radioactivity in the form of either free $^{125}$I or $^{125}$I-uracil.

FIG. 3A: Effects of the treatment time on the uptake of GPAID by BE(2)-C and SK-N-SH cells. FIG. 3B: Concentration-dependent uptake of GPAID by BE(2)-C and SK-N-SH cells after 1-hour treatment. FIG. 3C: Total $^{125}$I intracellular disintegrations accumulated over 24 hours after incubation of BE(2)-C and SK-N-SH cells with various concentrations of GPAID for 1 hour. * indicates an estimated systemic concentration of $^{131}$IMIBG in a 20-kg child at the lowest clinically used dose of 5 GBq. Arrow points to D37 of 8.7 disintegrations per cell reported for $^{125}$I incorporated into DNA of human cells. FIG. 3D: Subcellular distribution of GPAID in neuroblastoma cells after various treatment times at the average GPAID concentration of 28±5 kBq/ml. FIG. 3E: Comparison of the cytoplasmic and nuclear distribution of GPAID and $^{125}$IMIBG in N1E-115 cells after a 24-hour treatment at an average concentration of 29±3 kBq/ml. Nearly 100% of $^{125}$I activity in the nuclei of cells treated with GPAID is bound to DNA. FIG. 3F: Cellular uptake of GPAID by BE(2)-C cells in the absence (grey bars) and the presence (black bars) of 0.05-mM nonradioactive MIBG. FIG. 3G: Cellular uptake of GPAID by SK-N-SH cells in the absence (grey bars) and the presence (black bars) of 0.05-mM nonradioactive MIBG. FIG. 3H: Survival of BE(2)-C cells exposed to GPAID without (grey symbols) and with (black symbols) 0.05 mM nonradioactive MIBG. FIG. 3I: Colonies of BE(2)-C cells 3 weeks after treatment: Top: Control cells treated with MIBG alone; and Bottom: Cells treated with 25.8±0.7 kBq/ml GPAID for 24 hours. FIG. 3J: ImageJ analyses of colonies shown in FIG. 3I. FIG. 3K: Survival of SK-N-SH cells exposed to GPAID without (grey symbols) and with (black symbols) 0.05-mM nonradioactive MIBG.

FIG. 4A: Weights of intraperitoneal N1E-115 tumors extirpated from control mice (black bar) and from mice treated with an average dose of 3.64±0.10 MBq per mouse GPAID (grey bar). FIG. 4B: Residual levels of $^{125}$I in various tissues and tumors extirpated from mice treated with GPAID at the termination necropsy 14 days after treatment. FIG. 4C: Hemoglobin values in tumor-bearing controls NT (black bar) and mice treated with GPAID (grey bar). FIG. 4D: Hematocrit values in tumor-bearing controls NT (black bar) and mice treated with GPAID (grey bar). Values for normal healthy mice are indicated by a short horizontal line with the standard deviation.

DETAILED DESCRIPTION OF THE INVENTION

Figure 1:
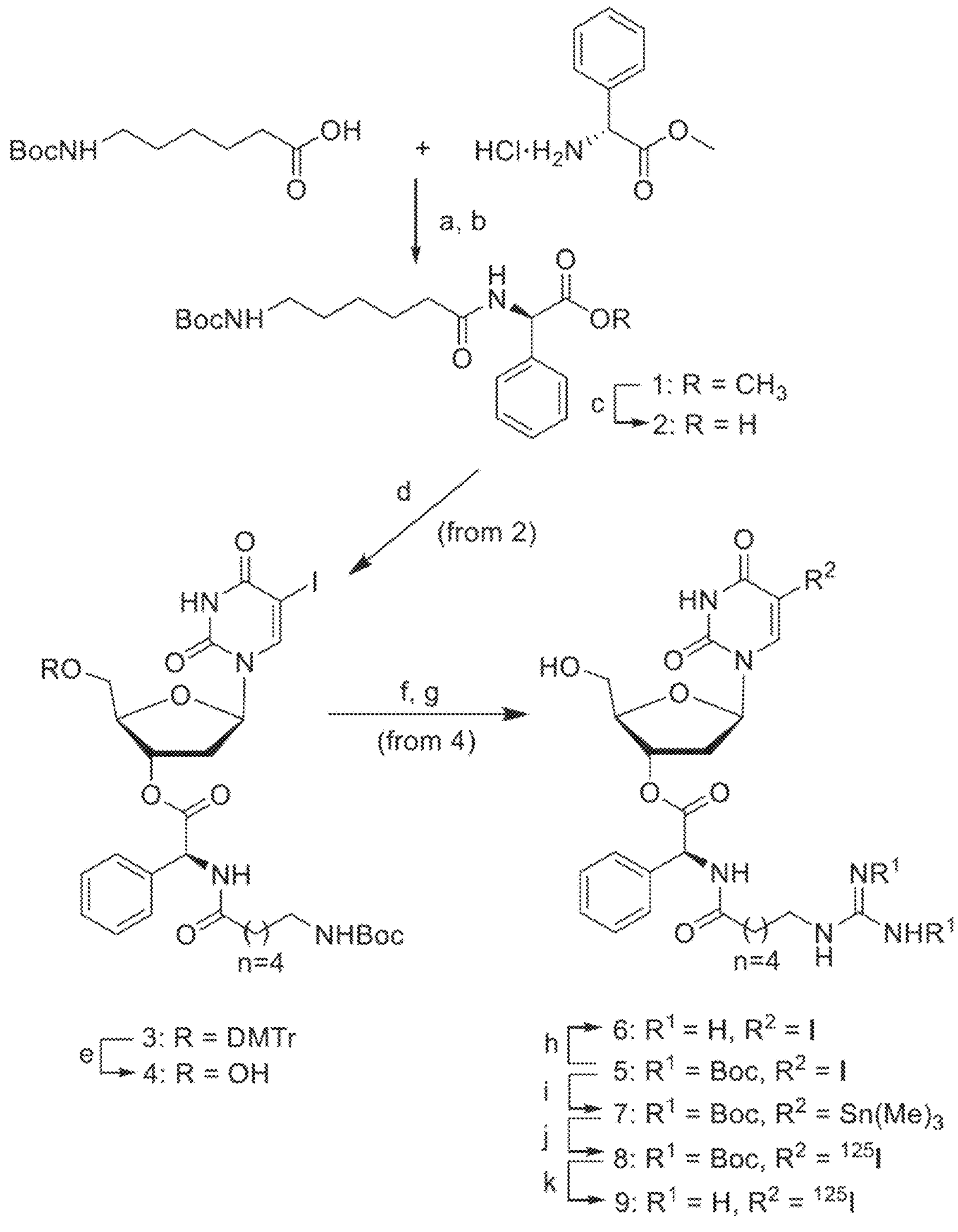
FIG. 1 provides a schematic for the synthesis of the indicated compounds. Reagents and conditions: a) 0° C. to 25° C., activated by 2-chloro-1,3-dimethyl-2-hexafluorophosphate (CIP)/N,N-dimethylaminopyridine (DMAP) in the presence of N,N-diisopropylethylamine (DIPEA); 88% yield after 2 hours; b) silica gel column chromatography; c) (1) MeOH/$H_2O$ (3:1, v/v), KOH (1.6 equiv), 3-5 hours at room temperature (rt); (2) 10% HCl, pH~2; d) (1) 5'-O-DMTr-2'-IUdR, (R)-(−)-2-[6-N-Boc-amino) hexanamido]-2-phenylacetic acid 2, dicyclohexylcarbodiimide (DCC)/DMPA in dichloromethane (DCM), 4 hours at rt; (2) silica gel column chromatography; e, f) $ZrCl_4$ (1 equiv), $CH_3CN$, 15 minutes, rt; 83% yield of 4; g) (1) 4 in ~25% TFA/DCM, rt; (2) evaporation under a vacuum at rt, treated with 15 ml of EtOAc/hexane (1:1, v/v) and sonicated; (3) washed with $Et_2O$, TFA salt dried under a high vacuum; (4) N,N'-bis (tertbutoxycarbonyl)-N"-trifluoromethanesulfonyl guanidine (1.1 equiv), TEA (2.2 equiv), 0° C. to rt, 6 hours; (5) 5% citric acid and saturated brine, dried over $MgSO_4$; (vi) silica gel column; 69% of 5; h) (1) TFA (0.1 ml) at rt~15 minutes; (2) evaporation with a stream of nitrogen, residue triturated with EtOAc and $Et_2O$; (3) TFA salt of 6 under a high vacuum to give 6 as white rigid foam; i) $Sn_2(CH_3)_6$, (1.25-s1.70 equiv) in $CH_3CN$, TEA (2-4 equiv), $(Ph_3P)Pd$ (II)$Cl_2$ (0.06-0.10 equiv), refluxed under nitrogen (1-3 hours); j) $Na^{125}I$ in NaOH (22.2-148 MBq), 30% $H_2O_2$ (5 μl), TFA/$CH_3CN$ (0.1% v/v), 1-minute sonication, 6- to 15-minutes reaction time, high-performance liquid chromatography (HPLC) purification; k) TFA (neat, 100 μl), sealed vial at 55-65° C., 20-35 minutes, average radiochemical yield>80%.

Herein, novel radioactive drugs, particularly for the treatment and/or detection of cancer (e.g., neuroblastoma (NB)), particularly in children, are provided. Targeted molecular radiotherapy with $^{131}$I-metaiodobenzylguanidine ($^{131}$I-MIBG), a treatment option for patients with relapsed or refractory NB, takes advantage of the intrinsic radiosensitivity of this malignancy (Deacon, et al. (1985) Radiother. Oncol., 3(3):201-209; Wheldon, et al. (1985) Br. J. Radiol., 58(691):661-664). $^{131}$IMIBG was introduced nearly 30 years ago (Kimmig, et al. (1984) J. Nucl. Med., 25(7):773-775). At present, it is used only in clinical trials because its place in the management of NB remains uncertain and it still needs the Food and Drug Administration (FDA) approval for high-risk NB (Gaze, et al. (2013) Q J Nucl Med Mol Imaging, 57(1):66-78; Wilson, et al. (2014) Eur. J. Cancer 50(4):801-815). This treatment has been shown to be relatively safe, but complete tumor responses are rare (Wilson, et al. (2014) Eur. J. Cancer 50(4):801-815). Side effects include hematologic toxicities, secondary malignancies, damage to ovaries, and thyroid disorders affecting >80% of the long-term survivors treated with $^{131}$IMIBG (Bleeker, et al. (2013) Eur J Nucl Med Mol Imaging. 2013; 40(11):1711-1717; Polishchuk, et al. (2011) Cancer 117(18):4286-4293; Incesoy-Ozdemir, et al. (2011) Turk J Pediatr., 53(1):83-86; Garaventa, et al. (2003) Cancer 97(5):1332-1338; Clement, et al. (2014) J Clin Endocrinol Metab., 99(1):E112-E116; Clement, et al. (2013) Pediatr Blood Cancer, 60(11):1833-1838).

A series of norepinephrine transporter-targeted (NET) and DNA co-targeted theranostics to ameliorate these deficiencies of MIBG has been developed (Kortylewicz, et al. (2020) J Med Chem., 63:2051-2073; U.S. Pat. No. 10,874,752). Employing Auger electron emitters such as $^{123}$I, $^{124}$I, or $^{125}$I yields agents that are virtually harmless when located in the cytoplasm or extracellular spaces but are extraordinarily radiotoxic when either within the structure of DNA or in its immediate vicinity. Nearly all of the electron energy associated with the $^{125}$I decay is deposited within a sphere smaller than the cell nucleus (Booz, et al. (1987) Radiat Environ Biophys., 26(2):151-162; Adelstein, et al. (1987) Int J Rad Appl Instrum B., 14(3):165-169). The Auger electron-emitting drugs enter NB cells by the same mechanism as MIBG and are subsequently catabolized to a product that can participate in the DNA synthesis, scheduled or unscheduled (Kortylewicz, et al. (2020) J Med Chem., 63:2051-2073). With this dual-target approach, therapeutic radiation doses can be delivered to NB cells while sparing normal tissues. A potential clinical candidate 5-[$^{125}$I]iodo-3'-O-(ε-guanidinohexanoyl)-2'-deoxyuridine (IDG) has been described, but its half-life in human serum was relatively short (~2.3 hours). The lengthening of biological half-lives can produce more effective theranostics (Chen, et al. (2017) J Nucl Med., 58(4):590-597; Bandara, et al. (2018) Bioconjug Chem., 29(7):2448-2454).

Herein, with the intention to increase biological stability, (R)-(−)-5-iodo-3'-O-[2-(F-guanidinohexanoyl)-2-phenylacetyl]-2'-deoxyuridine (GPAID) was prepared and evaluated. The addition of a bulky phenylacetyl group provides steric hindrance of the 3'-ester. Moreover, D-enantiomers of natural amino acids are not recognized by most mammalian enzymes and thereby exhibit increased enzymatic stability. For instance, D-amino acid esters are hydrolyzed >70 times slower than the corresponding esters of L-amino acids (Guichard, et al. (1994) Proc Natl Acad Sci USA, 91(21): 9765-9769; Tamura, et al. (1996) Pharm Res., 13(11):1663-1667; Vig, et al. (2003) Pharm Res., 20(9):1381-1388; Tsume, et al. (2014) Eur J Pharm Biopharm., 86(3):514-523). Properties of the new derivative were evaluated in vitro using NB cell lines and in vivo in NB allografts in mice. GPAID targets NB cells in the same way as MIBG and also co-targets DNA of proliferating cells, an attribute especially advantageous in the treatment of MYCN-amplified tumors. The data indicate that GPAID is effective to treat cancers such as NB, particularly high risk NB or refractory disease.

In accordance with the instant invention, norepinephrine transporter (NET) and DNA co-targeted compounds are provided. In certain embodiments, the compounds of the instant invention are of Formula (I):

(I)

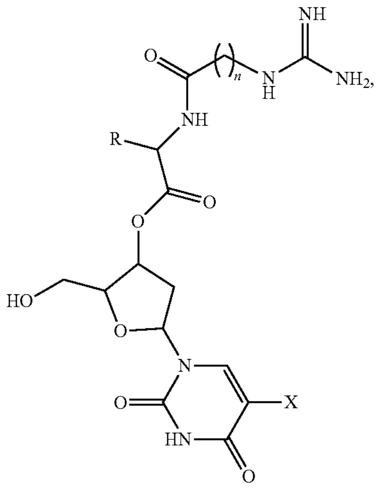

wherein X is a radionuclide (e.g., radioisotope) or a chelating agent (optionally attached via a linker) comprising a radionuclide; R is an optionally substituted aryl or heteroaryl; and n=1-5, including pharmaceutically acceptable salts and stereoisomers thereof. In certain embodiments, X is a radionuclide. In certain embodiments, the radionuclide is an alpha-emitter (e.g., $^{212}$Pb, $^{212}$Bi, $^{213}$Bi, $^{223}$Ra, $^{225}$Ac, etc.), beta-emitter (e.g., $^{64}$Cu, $^{86}$Y, $^{89}$Sr, $^{89}$Zr, $^{90}$Y, $^{124}$I, $^{131}$I, $^{177}$Lu, $^{188}$Re, etc., particularly $^{124}$I or $^{131}$I), gamma-emitter, positron-emitter, or Auger electron-emitter (e.g., $^{77}$Br, $^{111}$In, $^{123}$I, $^{125}$I, etc., particularly $^{77}$Br, $^{123}$I, or $^{125}$I). In certain embodiments, the radionuclide is an Auger electron-emitting radionuclide. In certain embodiments, the radionuclide is a positron emission tomography (PET) compatible radionuclide. In certain embodiments, the radionuclide is a single photon emission computed tomography (SPECT) compatible radionuclide. In certain embodiments, the radionuclide is a radiohalogen. In certain embodiments, the radionuclide is selected from the group consisting of $^{123}$I, $^{124}$I, $^{125}$I, $^{131}$I, $^{211}$At, $^{18}$F, $^{76}$Br, $^{77}$Br, and $^{80m}$Br. In certain embodiments, the radionuclide is a radioactive iodine. In certain embodiments, the radionuclide is selected from the group consisting of $^{123}$I, $^{124}$I, and $^{125}$. In certain embodiments, n=5. In certain embodiments, R is aryl. In certain embodiments, R is phenyl. In certain embodiments, the aryl or heteroaryl is substituted by at least one $C_1$-$C_3$ alkyl (e.g., methyl), $C_2$-$C_4$ alkenyl, $C_1$-$C_3$ alkoxy (e.g., methoxy), $C_1$-$C_3$ monoalkylamino (—NH(alkyl)), $C_1$-$C_3$ dialkylamino (—N(alkyl)$_2$), halogen, —OH, —SH, —$NH_2$, —COOH, —CN, and/or —$NO_2$.

In certain embodiments, the compounds of the instant invention are of Formula (II):

(II)

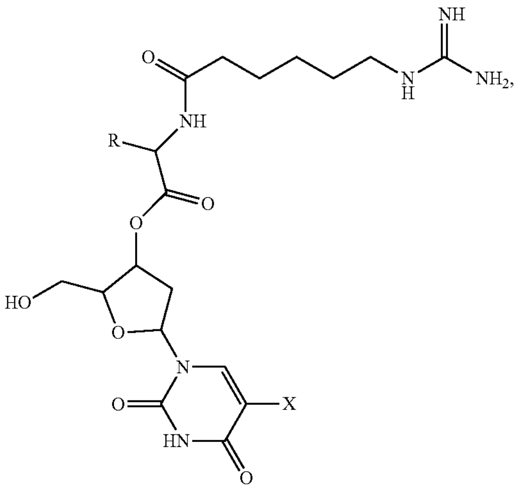

wherein X is a radionuclide (e.g., radioisotope) or a chelating agent (optionally attached via a linker) comprising a radionuclide, and R is an optionally substituted aryl or heteroaryl, including pharmaceutically acceptable salts and stereoisomers thereof. In certain embodiments, X is a radionuclide. In certain embodiments, the radionuclide is an alpha-emitter (e.g., $^{212}$Pb, $^{212}$Bi, $^{213}$Bi, $^{223}$Ra, $^{225}$Ac, etc.), beta-emitter (e.g., $^{64}$Cu, $^{86}$Y, $^{89}$Sr, $^{89}$Zr, $^{90}$Y, $^{124}$I, $^{131}$I, $^{177}$Lu, $^{188}$Re, etc., particularly $^{124}$I or $^{131}$I) gamma-emitter, positron-emitter, or Auger electron-emitter (e.g., $^{77}$Br, $^{111}$In, $^{123}$I, $^{125}$I, etc., particularly $^{77}$Br, $^{123}$I, or $^{125}$I). In certain embodiments, the radionuclide is an Auger electron-emitting radionuclide. In certain embodiments, the radionuclide is a positron emission tomography (PET) compatible radionuclide. In certain embodiments, the radionuclide is a single photon emission computed tomography (SPECT) compatible radionuclide. In certain embodiments, the radionuclide is a radiohalogen. In certain embodiments, the radionuclide is selected from the group consisting of $^{123}$I, $^{124}$I, $^{125}$I, $^{131}$I, $^{211}$At, $^{18}$F, $^{76}$Br, $^{77}$Br, and $^{80m}$Br. In certain embodiments, the radionuclide is a radioactive iodine. In certain embodiments, the radionuclide is selected from the group consisting of $^{123}$I, $^{124}$I, and $^{125}$I. In certain embodiments, R is aryl. In certain embodiments, R is phenyl. In certain embodiments, the aryl or heteroaryl is substituted by at least one $C_1$-$C_3$ alkyl (e.g., methyl), $C_2$-$C_4$ alkenyl, $C_1$-$C_3$ alkoxy (e.g., methoxy), $C_1$-$C_3$ monoalkylamino (—NH(alkyl)), $C_1$-$C_3$ dialkylamino (—N(alkyl)$_2$), halogen, —OH, —SH, —$NH_2$, —COOH, —CN, and/or —$NO_2$.

In certain embodiments, the compounds of the instant invention are of Formula (III):

(III)

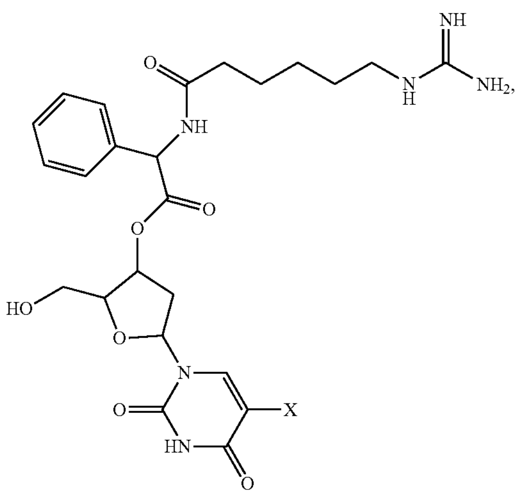

wherein X is a radionuclide (e.g., radioisotope) or a chelating agent (optionally attached via a linker) comprising a radionuclide, including pharmaceutically acceptable salts and stereoisomers thereof. In certain embodiments, X is a radionuclide. In certain embodiments, the radionuclide is an alpha-emitter (e.g., $^{212}$Pb, $^{212}$Bi, $^{213}$Bi, $^{223}$Ra, $^{225}$Ac, etc.), beta-emitter (e.g., $^{64}$Cu, $^{86}$Y, $^{89}$Sr, $^{89}$Zr, $^{90}$Y, $^{124}$I, $^{131}$I, $^{177}$Lu, $^{188}$Re, etc., particularly $^{124}$I or $^{131}$I), gamma-emitter, positron-emitter, or Auger electron-emitter (e.g., $^{77}$Br, $^{111}$In, $^{123}$I, $^{125}$I, etc., particularly $^{77}$Br, $^{123}$I, or $^{125}$I). In certain embodiments, the radionuclide is an Auger electron-emitting radionuclide. In certain embodiments, the radionuclide is a positron emission tomography (PET) compatible radionuclide. In certain embodiments, the radionuclide is a single photon emission computed tomography (SPECT) compatible radionuclide. In certain embodiments, the radionuclide is a radiohalogen. In certain embodiments, the radionuclide is selected from the group consisting of $^{123}$I, $^{124}$I, $^{125}$I, $^{131}$I, $^{211}$At, $^{18}$F, $^{76}$Br, $^{77}$Br, and $^{80m}$Br. In certain embodiments, the radionuclide is a radioactive iodine. In certain embodiments, the radionuclide is selected from the group consisting of $^{123}$I, $^{124}$I and $^{125}$I.

Chelating agents (e.g., metal chelators) are well known in the art (e.g., Liu et al. (2010) Materials 3(5): 3204-3217; Speer, T. W., *Targeted radionuclide therapy*, Wolters Kluwer Health/Lippincott Williams & Wilkins, 2011). In certain embodiments, the chelating agent is added to the compound via a bifunctional chelating agent (BFC). Examples of chelating agents include, without limitation: mercaptoacetyltriglycine ($MAG_3$), 1,4,7,10-tetraazacyclododecane-N,N',N",N'"-tetraacetic acid (DOTA), diethylenetriamene pentaacetate (DTPA), 6-hydrazinopridine-3-carboxylic acid (Hynic), 1-N-(4-aminobenzyl)-3,6,10,13,16,19-hexaazabicyclo[6.6.6] eicosane-1,8-diamine (SarAr), N'-{5-[Acetyl (hydroxy)amino]pentyl}-N-[5-({4-[(5-aminopentyl)(hydroxy)ami-no]-4-oxobutanoyl}amino)pentyl]-N-hydroxysuccinamide (DFO or deferoxamine), 1,4,7-triazacyclononane-N,N',N"-triacetic acid (NOTA), 2,2',2",2'"-(ethane-1,2-diyldinitrilo)tetraacetic acid (EDTA), 1,4,7,10,13,16-hexaazacyclooctadecane-N,N',N",N'",N"",N'""-hexaacetic acid (Heha), and the like.

As will be apparent to those skilled in the art, the compounds of the present invention may have one or more asymmetric centers or chiral centers, and in that case, exist in various stereoisomeric forms. The compounds of the present invention encompass all such optical isomers, diastereomers and enantiomers. The compounds may be prepared as a racemic mixture or racemate and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms from a mixture of enantiomers. Specific stereoisomers can be prepared by stereospecific synthesis using enantiomerically pure or enantiomerically enriched starting materials. The specific stereoisomers of either starting materials or products can be resolved and recovered by techniques known in the art, such as, without limitation, resolution of racemic forms, normal, reverse-phase, and chiral chromatography, recrystallization, enzymatic resolution, or fractional recrystallization of addition salts formed by reagents used for that purpose.

As explained herein, compounds of the instant invention are useful for the targeted treatment and/or imaging or detecting of cancers and conditions expressing norepinephrine transporter. In certain embodiments, the compounds of the instant invention are effective for killing cancer cells. In certain embodiments, the compounds of the instant invention generate a detectable signal.

In accordance with the instant invention, compositions and methods for inhibiting (e.g., reducing or slowing), treating, and/or preventing cancer in a subject are provided. In a particular embodiment, the methods comprise administering to a subject in need thereof at least one compound of the instant invention. In certain embodiments, the compound is of Formula (I), (II), or (III). The compounds of the present invention can be used to directly kill cancer cells. The compounds may also be used to increase the sensitivity of cancer cells, making them more susceptible to other therapeutics (e.g., chemotherapeutics, radiotherapy, etc.).

The methods of the instant invention can be used to inhibit, prevent, and/or treat any cancer in a subject in need thereof, particularly a human. In a particular embodiment, the cancer is a solid tumor. The cancer may be chemo-resistant and/or radio-resistant. In certain embodiments, the cancer expresses the norepinephrine transporter (e.g., SLC6A2; Gene ID: 6530). Examples of cancer that can be treated by the methods of the instant invention include, without limitation: breast cancer, colon cancer, bladder cancer, liver cancer, neuroendocrine tumor (e.g., gastrointestinal neuroendocrine tumor, pancreatic neuroendocrine tumor, etc.), neuroblastoma, brain cancers, head and neck cancer, lung cancer, esophageal cancer, ovarian cancer, stomach cancer, skin cancer, cervical cancer, endometrial cancer, testicular cancer, kidney cancer, carcinoid tumors, and bone cancer. In certain embodiments, the cancer is neuroblastoma.

The methods may further comprise the administration of at least one other cancer therapy to the subject. Examples of additional therapies include, without limitation: surgery (e.g., tumor excision), chemotherapies (chemotherapeutic agents), immunotherapies, cell therapies, targeted therapy (e.g., small molecule inhibitors, antibodies), radiosentizer, and radiation therapy (e.g., external beam radiation, ionizing radiation, radiopharmaceuticals). The compound of the instant invention may be administered to a subject consecutively (e.g., before and/or after) and/or simultaneously with another therapy for treating, inhibiting, and/or preventing the cancer in the subject. In a particular embodiment, the compound of the instant invention is administered with at least one chemotherapeutic agent.

Chemotherapeutic agents are compounds that exhibit anticancer activity and/or are detrimental to a cell (e.g., a toxin). Suitable chemotherapeutic agents include, but are not limited to: receptor tyrosine kinase inhibitors, toxins (e.g., saporin, ricin, abrin, ethidium bromide, diptheria toxin, *Pseudomonas* exotoxin, and others listed above; thereby generating an immunotoxin when conjugated or fused to an antibody); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase I inhibitor (e.g., topotecan); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate); pyrimidine antagonists (analogs) such as fluorouracil (5-fluorouracil), gemcitabine, fluorodeoxyuridine, CB3717, azacitidine, cytarabine, and floxuridine; purine antagonists (analogs) such as mercaptopurine, 6-thioguanine, fludarabine, pentostatin; asparginase; ribonucleotide reductase inhibitors (such as hydroxyurea); tubulin interactive agents (e.g., vincristine, vinblastine, docetaxel, and paclitaxel (Taxol®)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); immunomodulator (e.g., levamisole); and antihormonal antigens (e.g., tamoxifen, antiandrogen agents such as flutamide; and antiadrenal agents such as mitotane and aminoglutethimide).

Norepinephrine transporter is also involved in the pathophysiology and treatment of attention-deficit hyperactivity disorder (Hannestad, et al. (2010) Biol. Psychiatry 68:854-860), substance abuse (Ding, et al. (2010) Synapse 64: 30-38), neurodegenerative disorders (including Alzheimer's disease and Parkinson's disease) (Tejani-Butt, et al. (1993) Brain Res., 631:147-159; Rommelfanger, et al. (2007) Biochem Pharmacol, 74:177-190), and depression (Klimek, et al. (1997) J Neurosci, 17:8451-8458). Accordingly, compositions and methods for inhibiting (e.g., reducing or slowing), treating, and/or preventing attention-deficit hyperactivity disorder, substance abuse, neurodegenerative disorder, and/or depression in a subject are provided. In a particular embodiment, the methods comprise administering to a subject in need thereof at least one compound of the instant invention. In certain embodiments, the compound is of Formula (I), (II), or (III).

Compositions comprising at least one compound of the instant invention and at least one pharmaceutically acceptable carrier are encompassed by the instant invention. Such compositions may be administered to a subject to detect and/or image cancer. Such compositions may also be administered, in a therapeutically effective amount, to a patient in need thereof for the treatment of cancer. When an additional therapy is utilized in combination with the compound of the instant invention, the compound of the instant invention may be contained within a first composition with at least one pharmaceutically acceptable carrier and the additional therapy (e.g., chemotherapeutic agent) may be contained within a second composition with at least one pharmaceutically acceptable carrier (the carriers of the two compositions may or may not be the same). Alternatively, the composition may comprise both the compound of the instant invention and additional therapy (including a pharmaceutically acceptable carrier). Having the agents in separate compositions allows for ease of sequential and/or simultaneous administration. The instant invention also encompasses kits comprising at least one composition comprising at least one compound of the instant invention and at least one composition comprising at least one additional therapy (e.g., chemotherapeutic agent).

The compounds and compositions of the present invention can be administered by any suitable route, for example, by injection (e.g., for local (direct, including to or within a tumor) or systemic administration), or other modes of administration. The composition may be administered by any suitable means, including intratumoral, parenteral, intramuscular, intravenous, orally, intraarterial, intraperitoneal, subcutaneous, intraareterial, intrarectal, and intramuscular administration. In a particular embodiment, the compounds and compositions of the present invention are administered by direct injection (e.g., to the tumor and/or the surrounding area).

In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, PA Lippincott Williams & Wilkins. 2005. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. For example, the compounds may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the compounds in the chosen medium may be varied and the medium may be chosen based on the desired route of administration of the pharmaceutical preparation. Except insofar as any conventional media or agent is incompatible with the compounds to be administered, its use in the pharmaceutical preparation is contemplated.

Selection of a suitable pharmaceutical preparation depends upon the method of administration chosen. For example, the molecules of the invention may be administered by direct injection into any cancerous tissue or into the area surrounding the cancer. In this instance, a pharmaceutical preparation comprises the molecules dispersed in a medium that is compatible with the cancerous tissue.

As stated hereinabove, agents of the instant invention may also be administered parenterally by intravenous injection into the blood stream, or by subcutaneous, intramuscular, intratumor, intrathecal, or intraperitoneal injection. Pharmaceutical preparations for parenteral injection are known in the art. If parenteral injection is selected as a method for administering the molecules, steps should be taken to ensure that sufficient amounts of the molecules reach their target cells to exert a biological effect. The lipophilicity of the molecules, or the pharmaceutical preparation in which they are delivered, may have to be increased so that the molecules can arrive at their target locations. Methods for increasing the lipophilicity of a molecule are known in the art.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, topical, or parenteral. In preparing the molecule in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard chemotherapies. The dosage units of the molecules may be determined individually or in combination with each chemotherapy according to greater shrinkage and/or reduced growth rate of tumors.

The concentration of the compound of the instant invention in a composition can be determined by those of skill in the art, depending on the purpose of the administration of the compound. In certain embodiments, an effective amount of the compound for diagnostic applications will be an amount sufficient to provide between 0.1 mCi and 10 mCi of radioactivity. In certain embodiments, for diagnostic and/or detection purposes, the compound may be present in the composition from about 0.01 mCi/mL to about 100 mCi/mL, particularly about 0.1 mCi/mL to about 10 mCi/mL. For therapeutic purposes, the compounds of the instant invention should be present at a concentration to provide a therapeutically effective amount to the subject. In certain embodiments, a therapeutically effective amount will be a dose that provides from about 1 mCi (37 MBq)-20 mCi (740 MBq) of radioactivity per kg of the subject's body weight. In certain embodiments, for therapeutic purposes, the compound may be present in the composition from about 0.1 mCi/mL to about 1000 mCi/mL, particularly about 1 mCi/mL to about 100 mCi/mL or about 5 mCi/mL to about 20 mCi/mL. The concentrations of the compound in the composition may vary from or within these ranges based on mode of administration, proximity to cancer, and pharmaceutically acceptable carrier used.

The pharmaceutical preparation comprising the molecules of the instant invention may be administered at appropriate intervals, for example, at least once a day or more until the pathological symptoms are reduced or alleviated, after which the dosage may be reduced to a maintenance level. The appropriate interval in a particular case would normally depend on the condition of the patient.

In accordance with another aspect of the instant invention, methods of detecting a cancer and/or monitoring/tracking the progress of a cancer and/or its treatment are provided. Methods of diagnosing and/or prognosing cancer in a subject are also provided. The methods comprise administering at least one compound of the instant invention to the subject and detecting the presence of the compound in the subject. In a particular embodiment, the compound is administered to the tumor and/or its surrounding area. The cancer may be detected in vivo (e.g., imaged). In certain embodiments, the compound is imaged between about 0.25 hour and 1 week of administration, particularly within 1 day or within 1-3 hours. The methods can be used to detect if the administered compound is taken up by the cancerous tissue and/or the amount of the administered dose that is taken up by the cancerous tissue. This allows for the assessment of off-target toxicity and the efficacy of the therapy.

Methods of detecting attention-deficit hyperactivity disorder, substance abuse, neurodegenerative disorder, and/or depression and/or monitoring/tracking the progress of an attention-deficit hyperactivity disorder, substance abuse, neurodegenerative disorder, and/or depression and/or its treatment are provided. Methods of diagnosing and/or prognosing attention-deficit hyperactivity disorder, substance abuse, neurodegenerative disorder, and/or depression in a subject are also provided. The methods comprise administering at least one compound of the instant invention to the subject and detecting the presence of the compound in the subject. In a particular embodiment, the compound is administered directly. The attention-deficit hyperactivity disorder, substance abuse, neurodegenerative disorder, and/or depression may be detected in vivo (e.g., imaged). In certain embodiments, the compound is imaged between about 0.25 hour and 1 week of administration, particularly within 1 day or within 1-3 hours. The methods can be used to detect if the administered compound is taken up by the cell or tissue and/or the amount of the administered dose that is taken up by the cell or tissue. This allows for the assessment of off-target toxicity and the efficacy of the therapy.

In a particular embodiment, the compound administered to the subject comprises an isotope (e.g., one that can be detected). The isotope selected for the compound should match the detection technique used to image the subject. For example, when positron emission tomography (PET) is utilized for imaging the subject, a positron-emitting isotope (e.g., $^{13}N$, $^{18}F$, $^{68}Ga$, $^{89}Zr$, $^{82}Rb$, $^{124}I$, etc.) may be conjugated to the compound of the invention (i.e., the X group). When single photon emission computed tomography (SPECT) or scintigraphy is utilized for imaging the subject, a gamma-emitting isotope (e.g., $^{99m}Tc$, $^{111}In$, $^{123}I$, $^{131}I$, etc.) may be conjugated to the compound of the invention (i.e., the X group).

As stated hereinabove, the instant methods may be used to diagnose cancer in patient and/or determine the prognosis of a patient, including stage and grade (particularly whether it is metastatic) of a tumor and its potential sensitivity to therapy (e.g., resistance to a chemotherapeutic agent). Similarly, the methods may be used to determine the efficacy of a treatment of a patient (e.g., whether the tumor and/or metastases are decreasing due an administered treatment). The methods of the invention may be performed more than once over a period of time to monitor tumor volume and/or metastases. The decrease in tumor volume as determined by imaging is indicative of remission or a successful treatment, while the lack of change in tumor volume in a patient undergoing treatment may be indicative of resistance to the therapy and/or may indicate that a different therapeutic strategy could be employed. Similarly, the gain of tumor volume in a patient over time can be indicative of recurrence. In certain embodiments, the methods are used to identify the location of the main neuroblastoma tumor as well as any other tumors or metastases throughout other areas of the body.

DEFINITIONS

The following definitions are provided to facilitate an understanding of the present invention:

The singular forms "a," "an," and "the" include plural referents unless the context clearly dictates otherwise.

As used herein, the terms "host," "subject," and "patient" refer to any animal, including humans.

As used herein, "diagnose" refers to detecting and identifying a disease (e.g., cancer) in a subject. The term may also encompass assessing or evaluating the disease status (progression, regression, stabilization, response to treatment, etc.) in a patient known to have the disease.

As used herein, the term "prognosis" refers to providing information regarding the impact of the presence of cancer (e.g., as determined by the diagnostic methods of the present invention) on a subject's future health (e.g., expected morbidity or mortality, the likelihood of getting cancer and/or recurrence, drug resistance status of the cancer, and the risk of or presence of metastases). In other words, the term "prognosis" refers to providing a prediction of the probable course and outcome of a cancer or the likelihood of recovery from the cancer.

As used herein, the term "prevent" refers to the prophylactic treatment of a subject who is at risk of developing a condition (e.g., cancer or metastatic cancer) resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a cancer results in at least a reduction in the size of a tumor or cancerous tissue and/or reduction in the number and/or size of metastases.

A "therapeutically effective amount" of a compound or a pharmaceutical composition refers to an amount effective to prevent, inhibit, or treat a particular disorder or disease (e.g., cancer) and/or the symptoms thereof.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "radiosensitizer", as used herein, is defined as a molecule administered to animals in therapeutically effective amounts to increase the sensitivity of the cells to radiation. Radiosensitizers increase the sensitivity of cells to the toxic effects of radiation. Radiosensitizers include, without limitation, 2-nitroimidazole compounds, and benzotriazine dioxide compounds, halogenated pyrimidines, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

The term "aryl," as employed herein, refers to monocyclic and bicyclic hydrocarbon radicals containing 5 to 10 carbons in the ring system wherein at least one ring is aromatic. Aryl groups may be optionally substituted through available carbon atoms. Typically, an aryl group may have 1, 2, 3, or more substituents. In certain embodiments, the aryl is substituted by at least one $C_1$-$C_3$ alkyl (e.g., methyl), $C_2$-$C_4$ alkenyl, $C_1$-$C_3$ alkoxy (e.g., methoxy), $C_1$-$C_3$ monoalkylamino (—NH(alkyl)), $C_1$-$C_3$ dialkylamino (—N(alkyl)$_2$), halogen, —OH, —SH, —$NH_2$, —COOH, —CN, and/or —$NO_2$. Examples of aryl groups include, without limitation, phenyl, naphthyl (e.g., 1-naphthyl and 2-naphthyl), or indenyl.

The term "heteroaryl," as used herein, refers to an optionally substituted aryl that includes at least one (e.g., from 1 to about 4) sulfur, oxygen, or nitrogen heteroatom ring members. Examples of heteroaryl groups include, without limitation, pyridinyl, pyrazinyl, pyrimidinyl, purinyl, imidazolyl, furanyl, thiophenyl, pyrrolyl, etc.

The term "radiohalogen", as used herein, refers to an isotopic form of a halogen (e.g., F, Cl, Br, I, or At) that exhibits radioactivity. Examples of radiohalogens include, without limitation, $^{18}F$, $^{74}Br$, $^{75}Br$, $^{76}Br$, $^{77}Br$, $^{80m}Br$, $^{81}Br$, $^{123}I$, $^{124}I$, $^{125}I$, $^{127}I$, $^{131}I$, and $^{211}At$. In certain embodiments, the radiohalogen is selected from the group consisting of $^{123}I$, $^{124}I$, $^{125}I$, $^{131}I$, $^{211}At$, $^{18}F$, $^{76}Br$, $^{77}Br$, and $^{80m}Br$.

The term "alkoxy" refers to alkyl-O—, wherein the term "alkyl" refers to saturated straight and branched chain hydrocarbon radicals (e.g., having 1-8 carbon atoms, 1-6 carbon atoms, 1-4 carbon atoms, or 1-3 carbon atoms).

As used herein, a "linker" is a chemical moiety comprising a chain of atoms that covalently attach at least two compounds. The linker can be linked to any synthetically feasible position of the compounds, but preferably in such a manner as to avoid blocking the compound's desired activity. Linkers are generally known in the art. Exemplary linkers may comprise at least one optionally substituted; saturated or unsaturated; linear, branched or cyclic alkyl group or an optionally substituted aryl group. In a particular embodiment, the linker may contain from about 1 to about 50 atoms, about 1 to about 40 atoms, about 1 to about 30 atoms, or about 1 to about 25 atoms. The linker may also be a polypeptide. The linker may be non-biodegradable under physiological environments or conditions or cannot be cleaved under physiological environments or conditions.

The following example is provided to illustrate various embodiments of the present invention. The example is illustrative and is not intended to limit the invention in any way.

EXAMPLE

Neuroblastoma, the most common extracranial solid tumor in children, accounts for nearly 8% of childhood cancers in the United States. It is a disease with pronounced clinical and biological heterogeneities. The amplification of MYCN, whose key tumorigenic functions include the promotion of proliferation, facilitation of the cell's entry into the S phase, and prevention of cells from leaving the cell cycle, correlates with poor prognosis. Patients with a high proliferation index disease have low survival rates. Neuroblastoma is one of the most radioresponsive of all human tumors. To exploit this radiosensitivity, radioactive guanidine (R)-(−)-5-[$^{125}$I]iodo-3'-O-[2-(ε-guanidinohexanoyl)-2'-phenylacetyl]-20-deoxyuridine (9, GPAID) was designed. This compound enters neuroblastoma cells much like metaiodobenzylguanidine (MIBG). Additionally, it cotargets DNA of proliferating cells, an attribute especially advantageous in the treatment of MYCN-amplified tumors. GPAID was synthesized from the trimethylstannyl precursor with an average yield of >90% at the no-carrier-added specific activities. The norepinephrine transporter-aided delivery of GPAID to neuroblastoma cells was established in the competitive uptake studies with nonradioactive MIBG. The intracellular processing and DNA targeting properties were confirmed in the subcellular distribution experiments. Studies in a mouse model of neuroblastoma demonstrated the therapeutic potential of GPAID. The tin precursor of GPAID can be used to prepare compounds radiolabeled with single-photon emission computed tomography (SPECT)- and positron-emission tomography (PET)-compatible radionuclides. Accordingly, these reagents can function as theranostics useful in the individualized and comprehensive treatment strategies comprising treatment planning and the assessment of tumor responses as well as the targeted molecular radiotherapy employing treatment doses derived from the imaging data.

Materials and Methods

General

Chemicals and reagents purchased from commercial suppliers were used without further purification, unless indicated. Sodium [$^{125}$I]iodide in $1\times10^5$ NaOH (pH 8-11), with specific activities of >78000 GBq/mmol was from PerkinElmer (Billerica, MA). Radioactivity was measured with Minaxi γ-counter (Packard, Waltham, MA) and a dose calibrator (CapIntec Inc., Ramsey, NJ). Analytical TLC was carried out on plastic plates precoated with a 0.2-mm layer of silica (normal phase Merck 60 $F_{254}$, Sigma-Aldrich, St. Louis, MO). Spots were visualized with either short wave UV or iodine vapors. Flush column chromatography was performed using Merck silica gel 60 as a stationary phase. Compounds were resolved and their purity evaluated by the HPLC analyses conducted on Gilson (Middleton, WI) and ISCO (Lincoln, NE) systems, with 5-μm, 250×4.6 mm analytical columns, either Columbus C8 or C18 (Phenomenex, Torrance, CA) and ACE C18 (Advanced Chromatography Technologies, ace-hplc.com). Columns protected by guard filters were eluted at a rate of 0.8 mL/minute with various gradients of $CH_3CN$ (10-95%) in water, with or without TFA (0.07%, w/v). Two variable wavelength UV detectors: UVIS-205 (Linear, Irvine, CA) and UV116 (Gilson) were used, jointly with the sodium iodide crystal Flow-count radioactivity detector (Bioscan, Washington, DC), connected to the outlet of UV detector. Both signals were monitored and analyzed simultaneously. All the target nonradioactive compounds were found to be ≥98% pure by the rigorous HPLC analysis, with the integration of a peak area (detected at 220 and/or 280 nm). Radioiodinated products were identified and evaluated through the independently prepared non-radioactive reference compounds, by comparing UV signals of the non-radioactive standards with signals from radio-TLC ($R_f$) and radio-HPLC ($t_R$) of the radioactive products. Before testing the biological activities and stability, each final target compound was once again purified by HPLC using linear gradient of EtOH (0-70%) in phosphate buffer (10 mM, pH 6.1) to eliminate the presence of TFA and $CH_3CN$ in tested samples. All radiolabeled products, if kept in a solution overnight at ambient temperature, were purified one more time shortly before conducting further experiments, although the HPLC analysis rarely indicated less than 95% of the radiochemical purity. Solutions containing the product were evaporated with a stream of nitrogen and reconstituted in a preferred solvent at the required concentration and then filtered through a sterile 0.2-μ filter (Millipore) into a sterile evacuated vial. $^1H$, $^{13}C$ NMR spectra were recorded in $(CD_3)_2SO$, $CDCl_3$ and $CD_3OD$ at ambient temperature on Bruker Avance III HD 600 MHz spectrometer. All NMR analyses were performed at the University of Nebraska Medical Center Eppley Institute NMR Facility (Omaha, NE). Chemical shifts are given as δ (ppm) relative to TMS as internal standard with Jin hertz. Deuterium exchange and decoupling experiments were performed to further assist signals assignments of protons. High resolution electrospray ionization (ESI-HR) mass spectra (in positive mode) were acquired on a Waters Synapt G2 HDMS mass spectrometer at the Washington University Resource for Biomedical and Bio-organic Mass Spectrometry (St. Louis, MO).

Chemistry

(R)-(−)2-[6-(tert-butoxycarbonylamino)hexanamido]-2-phenylacetate (1)

Preparation of 1 through the coupling of 6-Boc-aminocaproic acid with (R)-(−)-2-phenylglycine methyl ester hydrochloride (H-D-Phg-OMe·HCl) was done with activation mediated by 2-chloro-1,3-dimethyl-2-hexafluorophosphate (CIP)/DMAP in the presence of DIPEA and provided Boc-6-Ahx-D-Phg-OMe (1) in 80% yield, without detectable racemization. With conventional DCC/DMAP activation, this coupling resulted in low isolation (48%) of the product with its isomerization (~20%), estimated by HPLC. To the stirred suspension of 6-Boc-aminocaproic acid (1.20 g, 5.19 mmol) in DCM (16 mL) in an ice bath were added DMAP (0.128 g, 1.05 mmol), DIPEA (2.7 mL, 15.56 mmol), CIP (2.60 g, 9.33 mmol) and (R)-(−)-2-phenylglycine methyl ester hydrochloride (1.26 g, 6.23 mmol). The mixture was stirred at 25° C. for 2 h and the solvent was evaporated under a vacuum at 40° C. The residue extracted with EtOAc was washed with 5% citric acid, 5% $NaHCO_3$ and water. The organic layer was dried ($MgSO_4$), the solvent evaporated and a crude product purified by column chromatography on a silica gel with a mixture of MeOH in DCM (0.6/10, v/v) followed by precipitation with EtOAc/hexanes to give 2.15 g (88% yield) of the (R)-(−)methyl 2-[6-(tert-butoxycarbonylamino)hexanamido]-2-phenylacetate as a white solid; recrystallized from EtOAc/hexanes mp 119-121° C.; $R_f$ value 0.42 (DCM/MeOH, 10:0.5). HPLC analysis: $t_R$=34.9 minutes (≥94.6% pure at 254/280 nm) on ACE C18 100 Å, (5 μm, 4.6×250 mm) column, at the elution rate of 0.8 mL/minute with a linear gradient of MeCN in water from 10 to 95% over 45 minutes, then 95% MeCN kept for 15 minutes. $^1$H NMR (DMSO-$d_6$, 500 MHz) δ: 10.60 (br s, 1H, NH), 8.54 (br s, 1H, NH), 7.26-7.21 (m, 5H, aryl), 5.79 (d, 1H, J=5.2 Hz, H2), 3.66 (s, 3H, C(O)OCH3), 3.16-3.11 (m, 2H, H6), 2.17-2.11 (m, 2H, H2), 1.58-1.52 (m, 2H, H5), 1.34 (s, 9H, CH3), 1.29-1.23 (m, 4H, H, H4).

(R)-(−)-2-[6-(tert-butoxycarbonylamino) hexanamido]-2-phenylacetic acid (2)

A dried out 1 (2.10 g, 5.55 mmol) dissolved in a mixture of MeOH/$H_2O$ (15 mL, 3:1, v/v) containing KOH (0.35 g, 6.24 mmol) was stirred at room temperature overnight. Methanol was evaporated under a vacuum and an aqueous phase acidified with 10% hydrochloric acid (pH~2) and a formed solid extracted with EtOAc (30 mL). An organic layer washed with brine was dried ($MgSO_4$) and the solvent evaporated, to give 1 (1.85 g, 91% yield) as a white solid; $R_f$ value 0.22 (DCM/MeOH, 10:0.5). HPLC analysis: $t_R$=17.2 minutes (≥9.6% pure at 254/280 nm) on ACE C18 100 Å, (5 μm, 4.6×250 mm) column, at the elution rate of 0.8 mL/minute with a linear gradient of MeCN in water from 10 to 95% over 45 minutes, then 95% MeCN kept for 15 minutes. $^1$H NMR (DMSO-$d_6$, 500 MHz) δ: 11.71 (s, 1H, COOH), 9.54 (br s, 1H, NH), 7.27-7.18 (m, 5H, aryl), 5.78 (d, 1H, J=5.2 Hz, H2), 3.18-3.14 (m, 2H, H6), 2.14-2.10 (m, 2H, H1), 1.58-1.51 (m, 2H, H5), 1.37 (s, 9H, 3×$CH_3$), 1.34-1.29 (m, 4H, H4, H3).

(R)-(−)-5-Iodo-5'-O-dimethoxytrityl-3'-O-[2-(ε-(N, N'-bis(tert-butyloxycarbonyl) guanidino)hexanoyl)-2-phenylacetyl]-2'-deoxyuridine (3)

To a solution of 5-iodo-5'-O-DMTr-2'-deoxyuridine (2.16 g, 3.29 mmol), (R)-(−)-2-[6-N-Boc-amino)hexanamido]-2-phenylacetic acid (2) (1.28 g, 3.51 mmol) and DMAP (0.087 g, 0.71 mmol) in 25 ml of DCM, dicyclohexylcarbodiimide (0.72 g, 3.49 mmol) were added at room temperature. The reaction mixture was stirred for 4 hours and filtered, and the solvent was removed under reduced pressure. The residue was purified by column chromatography on a silica gel using a gradient of MeOH in DCM (0.3-0.5:10), to give 2.22 g (67% yield) of 3 as a pale yellow solid; $R_f$=0.71 (DCM/MeOH, 10:0.5). HPLC analysis: $t_R$=34.1 minutes (≥97.1% pure at 254 and 280 nm) on ACE C18 100-Å column, (5 m, 4.6×250 mm) at the elution rate of 0.8 ml/minute with a linear gradient of MeCN in water from 50% to 95% over 90 minutes, then 95% MeCN kept for 10 minutes. $^1$H NMR (CDCl3, 600 MHz) δ 10.34 (s, 1H, H3-uridine), 8.39 (s, 1H, H6-uridine), 7.88-7.79 (m, 2H, HN-Boc, HN3), 7.43-7.27 (m, 10H, 2×5H, aryl; 4H, 2×H2-aryl-OMe, 2×H6-aryl-OMe), 6.84-6.79 (m, 4H, 2×H3-aryl-OMe, 2×H5-aryl-OMe), 6.28 (dd, H1', $^3J_{1',2'}$=6.45 Hz, $^3J_{1',2''}$=4.40 Hz), 5.35-5.28 (m, 1H, H2), 5.35-5.28 (m, 1H, H3'), 4.66-3.86 (m, 3H, H4', H5'), 3.78 (s, 6H, 2×OCH3-DMTr), 3.21-3.17 (2H, H9), 2.34-2.27 (m, 2H, H2'), 2.20-2.12 (m, 2H, H5), 1.85-1.64 (m, 2H, H8), 1.43 (s, 9H, 3×$CH_3$-t-butyl), 1.43-1.28 (m, 4H, H6, H7) ppm. HR-MS (ESI), (m/e): $[M+H]^+$ calculated for $[C_{49}H_{55}IN_4O_{11}+1H]^-$, 1003.2985; found 1003.2977.

(R)-(−)-5-Iodo-3'-O-[2-(ε-(N,N'-bis(tert-butyloxycarbonyl)guanidino)hexanoyl)-2-phenylacetyl]-2'-deoxyuridine (4)

Anhydrous 3 (1.81 g, 1.81 mmol) was dissolved in MeCN (10 ml), and $ZrCl_4$ (0.51 g, 2.19 mmol) was added. The mixture was stirred at room temperature for ~1 hour. The solvent was evaporated in a vacuum. Fifty milliliters of EtOAc/water mixture (1/1, v/v) were added to the residue and briefly sonicated. The organic layer was separated, washed with brine, and dried over $MgSO_4$. After evaporation of the solvent, a crude product was purified on a silica gel column to give 1.05 g (83% yield) of the title compound; $R_f$=0.43 (DCM/MeOH, 10:0.5). HPLC analysis: $t_R$=32.5 minutes (≥96.6% pure at 254 and 280 nm) on Jupiter C18 100-Å column (5 m, 4.6×250 mm) at the elution rate of 0.8 ml/minute with a linear gradient of MeCN in water from 10% to 95% over 45 minutes, then 95% MeCN kept for 15 minutes. $^1$H NMR ($CDCl_3$, 600 MHz) δ 10.56 (s, 1H, H3-uridine), 8.54 (s, 1H, H6-uridine), 802-7.87 (m, 2H, HN-Boc, HN3), 7.36-7.25 (m, 5H, aryl), 6.18 (dd, 1H, H1', $^3J_{1',2'}$=6.45 Hz, $^3J_{1',2'}$=4.40 Hz), 5.76-5.69 (m, 1H, H2), 5.35-5.18 (m, 2H, H3'-uridine, OH—C5'-uridine), 3.86-3.74 (m, 3H, H4'-uridine, H5'-uridine), 3.19-3.12 (2H, H9), 2.34-2.27 (m, 2H, H2'-uridine), 2.18-2.12 (2H, H5), 1.57-1.51 (2H, H8), 1.41 (s, 9H, 3×$CH_3$-t-butyl), 1.33-1.28 (4H, H6, H7) ppm. $^{13}$C NMR ($CDCl_3$, 100 MHz) δ: 172.3 (O═C4), 170.6 (O═C1), 163.5 (O═C4-uridine), 159.3 (0═C—O-t-butyl), 153.2 (O═C2-uridine), 145.3 (C6-uridine), 135.1 (C1-aryl), 129.3 (C2-aryl), 129.3 (C6-aryl), 128.5 (C3-aryl), 128.4 (C5-aryl), 127.3 (C4-aryl), 86.7 (C1'-uridine), 85.6 (C4'-uridine), 79.8 (C1-t-butyl), 76.2 (C3'-uridine), 68.8

(C5-uridine), 62.5 (C5'-uridine), 57.4 (C2), 40.8 (C9), 37.79 (C2'-uridine), 35.8 (C5), 28.4 (C8), 28.3 (C2-t-butyl), 26.2 (C7), 25.2 (C6). HR-MS (ESI), (m/e): $[M+H]^+$ calculated for $[C_{28}H_{37}IN_4O_9+1H]^+$, 701.1606; found 701.1611.

(R)-(−)-5-Iodo-3'-O-[2-(ε-(N,N'-bis (tert-butyloxy-carbonyl)guanidino)hexanoyl)-2-phenylacetyl]-2'-deoxyuridine (5)

The Boc group of 4 (1.33 g, 1.89 mmol) was cleaved with ~25% TFA in DCM. When reaction was completed (monitoring by thin layer chromatography [TLC]), the mixture was evaporated under a vacuum at room temperature. The oily residue was treated with 15 ml of EtOAc/hexane (1:1, v/v) and sonicated briefly a few times. The solvent was carefully decanted from solids, a crude product was washed with diethyl ether, and a solvent was drawn off again. This washing procedure was repeated, and then the remaining TFA salt was placed under a high vacuum to dry. The reaction vial containing a dried TFA salt suspended in DCM (15 ml) was placed on an ice bath, and TEA (278 μl, 2.0 mmol) was added to a stirred mixture immediately followed by N,N'-bis(tert-butoxycarbonyl)-N"-trifluoromethane-sulfonyl guanidine (0.83 g, 2.10 mmol). The mixture was stirred for 5 minutes, and a second portion of TEA (278 μl, 2.0 mmol) added to the resulting clear solution. The stirring continued for 6 hours (TLC monitoring) at room temperature. Upon the completion, an excess of amines and triflic amide was removed by aqueous workup with 5% citric acid and saturated brine. Organic phase was dried over $MgSO_4$, filtered, and evaporated. A crude product was purified on a silica gel column using a gradient of MeOH in DCM (0.8-2:10) to give 1.11 g of 5 in 69% yield. $R_f$=0.38 (DCM/MeOH, 10:0.8). HPLC analysis: $t_R$=36.9 minutes (≥95.7% pure at 254 and 280 nm) on ACE C18 100-Å column (5 m, 4.6×250 mm) at the elution rate of 0.8 ml/minute with a linear gradient of MeCN in water from 10% to 95% over 45 minutes, then 95% MeCN kept for 25 minutes. $^1H$ NMR ($CDCl_3$, 600 MHz) δ: 11.29 (s, 1H, HN3-uridine), 8.32-8.28 (m, 2H, Boc-NH— guanidine, HN3), 8.24 (s, 1H, H6-uridine), 7.40-7.36 (m, 5H, aryl), 6.36 (dd, 1H, H1'-uridine, $^3J_{1',2'}$=6.45 Hz, $^3J_{1',2''}$=4.20 Hz), 6.22-6.05 (m, 1H, H2), 5.54-5.38 (m, 2H, H3'-uridine, H4'-uridine), 4.22-3.82 (m, 3H, H5'-uridine, OH—C5'-uridine), 3.44-3.34 (m, 2H, H9), 2.60-2.56 (m, 1H, HN10-guanidine), 2.54-2.37 (m, 2H, H2'-uridine), 2.27-2.21 (2H, H5), 1.78-1.55 (m, 2H, H8), 1.46 (s, 9H, 3×$CH_3$-t-butyl), 1.41 (s, 9H, 3×$CH_3$-t-butyl), 1.40-1.35 (m, 4H, H6, H7) ppm. $^{13}C$ NMR ($CDCl_3$, 100 MHz) δ: 172.8 (O═C4), 170.63 (O═C1), 163.6 (O═C4-uridine), 159.6 (N═C—NH, guanidine), 156.2 (NC(O)—O-t-butyl, guanidine), 156.1 (HN—C(O)—O-t-butyl, guanidine), 153.3 (O═C2-uridine), 149.8 (C6-uridine), 135.1 (C1-aryl), 129.4 (C2-aryl), 129.2 (C6-aryl), 127.4 (C3-aryl), 127.4 (C5-aryl), 127.3 (C4-aryl), 86.3 (C1'-uridine), 85.2 (C4'-uridine), 83.2 (C1-t-butyl), 79.3 (C1-t-butyl), 76.0 (C3'-uridine), 68.6 (C5-uridine), 62.4 (C5'-uridine), 57.1 (C2), 40.8 (C9), 37.8 (C2'-uridine), 35.8 (C5), 28.3 (C8), 28.2 (d, C2-t-butyl), 28.1 (d, C2-t-butyl), 26.3 (C7), 25.2 (C6). HR-MS (ESI), (m/e): $[M+H]^+$ calculated for $[C_{34}H_{47}IN_6O_{11}+1H]^+$, 843.2420; found 843.2411.

(R)-(−)-5-Iodo-3'-O-[2-(ε-guanidinohexanoyl)-2-phenylacetyl]-2'-deoxyuridine (6)

A sample of this compound was prepared for use as the nonradioactive reference standard by the treatment of 5 (25 mg, 30 μmol) with TFA (0.1 ml) at room temperature for ~15 minutes. TFA was evaporated with a stream of nitrogen, the residue was triturated with ethyl acetate, briefly sonicated then evaporated again, and the residue was triturated with diethyl ether. The solvent was evaporated using a rotary evaporator, and the remaining TFA salt was kept under a high vacuum overnight to give 6 as white rigid foam. HPLC analyses: $t_R$=11.4 minutes (≥98.5% pure at 254 and 280 nm) on ACE C18 100-Å column, (5 m, 4.6×250 mm) eluted at 0.8 ml/minute with a linear gradient of MeCN in water; both solvents contained 0.07% TFA (v/v), first from 20% to 50% over 10 minutes, then to 95% MeCN during additional 10 minutes and eluting for further 15 minutes. $^1H$ NMR ($CD_3OD/D_2O$, 600 MHz) δ: 8.45 (s, 1H, H6-uridine), 8.24 (bs, 1H, HN3), 7.38-7.32 (m, 5H, aryl), 6.31 (dd, 1H, H1'-uridine, $^3J_{1',2'}$=6.40 Hz, $^3J_{1',2''}$=4.14 Hz), 6.12-6.03 (m, 1H, H2), 5.49-5.34 (m, 2H, H3'-uridine, H4'-uridine), 4.12-3.74 (m, 2H, H5'-uridine), 3.35-3.28 (m, 2H, H9, 2.54-2.37 (m, 2H, H2'-uridine), 2.27-2.21 (2H, H5), 1.68-1.47 (m, 2H, H8), 1.32-1.24 (m, 4H, H6, H7) ppm. HR-MS (ESI), (m/e): $[M+H]^+$ calculated for $[C_{24}H_{31}IN_6O_7+1H]^+$, 643.1336; found 643.2103.

(R)-(−)-5-Trimethylstannyl-3'-O-[2-(ε-(N,N'-bis(tert-butyloxycarbonyl) guanidino)hexanoyl)-2-phenylacetyl]-2'-deoxyuridine (7)

Stannylation of 5 was conducted in 30-ml MeCN twice: 244 mg (0.290 mmol) of 5 and repeated with 605 mg (0.718 mmol) of 5, using 165-mg (0.50 mmol) and 400-mg (1.22 mmol) hexamethylditin, respectively, with the palladium catalyst (~50 mg, 0.07 mmol) and TEA (200 μl, ~1.43 mmol) in both reactions. Each reaction mixture was gently refluxed under nitrogen for as long as the starting 5 was detectable (~3 hours). The reaction progress was checked by TLC. After cooling to ambient temperature, the mixture was filtrated through a thin pad of silica prewashed with EtOAc/hexanes (2:1; v/v) to separate the remaining catalyst. The filtrate was evaporated to dryness. Two major products were present: the desired trimethylstannane (high TLC mobility) and the protodestannylated form of starting iodide (slower on TLC). Crude products were separated and purified by repeating silica gel flash column chromatography with mixtures of EtOAc/hexanes (2:1-2:2, v/v) and/or various gradients of MeOH in DCM (0.3-0.7:10), to give 6 (94 and 278 mg) with 37% and 41% yields for the two reactions; $R_f$=0.55 (DCM/MeOH, 10:0.8). To reach ≥98% purity of stannylated product, the successive preparative HPLC purifications were required. Purified, anhydrous samples of stannane 7 in 100-μg aliquots were stored with the exclusion of light under nitrogen at −20° C. HPLC analyses: $t_R$=31.3 minutes (>98% pure at 254 and 280 nm) on ACE C18 100-A column (5 m, 4.6×250 mm) eluted at 0.8 ml/minute with a linear gradient of MeCN in water, first from 50% to 60% over 20 minutes, then to 70% MeCN during 10 minutes and increased to 95% MeCN in 15 minutes eluting for further 15 minutes. $^1H$ NMR ($CDCl_3$, 600 MHz) δ: 11.48 (s, 1H, HN3-uridine), 8.31 (bs, 1H, Boc-NH-guanidine), 803 (d, 1H, HN3, J=5.20 Hz), 7.85 (s, 1H, H6-uridine, $^3J_{Sn,H}$=8.36 Hz), 7.38-7.26 (m, 5H, aryl), 6.32 (dd, 1H, H1', $^3J_{1',2'}$=6.45 Hz, $^3J_{1',2''}$=4.20 Hz), 5.81-5.77 (m, 1H, H2), 4.23-4.18 (m, 1H, OH—C5'-uridine), 4.08-3.76 (m, 2H, H3'-uridine, H4'-uridine), 3.34-3.30 (m, 2H, H5'-uridine), 2.77-2.71 (m, 1H, HN10-guanidine), 2.66-2.59 (m, 2H, H9), 2.56-2.42 (m, 4H, H2'-uridine, H5), 2.32-2.29 (m, 2H, H8), 1.52 (s, 9H, 3×$CH_3$-t-butyl), 1.49 (s, 9H, 3×$CH_3$-t-butyl), 1.47-1.34 (m, 4H, H6, H7), 0.29 (s, 9H, 3×$SnCH_3I$, $^2J_{Sn,H}$=29.5 Hz) ppm. $^{13}C$ NMR ($CDCl_3$, 100

MHz) δ: 172.6 (O═C4), 170.7 (O═C1), 163.6 (C4-uridine), 160.3 (N═C—NH, guanidine), 158.2 (═NC(O)—O-t-butyl, guanidine), 157.1 (—HN—C(O)—O-t-butyl, guanidine), 150.7 (C2-uridine), 144.8 (C6-uridine), 135.4 (C1-aryl), 129.3 (C2-aryl), 129.3 (C6-aryl), 127.4 (C3-aryl), 127.3 (C5-aryl), 127.2 (C4-aryl), 113.3 (C5-uridine), 87.3 (C1'-uridine), 85.2 (C40-uridine), 83.1 (C1-t-butyl), 79.3 (C1-t-butyl), 76.2 (C3'-uridine), 62.7 (C5'-uridine), 56.9 (C2), 40.7 (C9), 36.9 (C2'-uridine), 35.8 (C5), 28.7 (C8), 28.3 (d, C2-t-butyl), 28.1 (d, C2-t-butyl), 26.2 (C7), 25.10 (C6), −9.3 ($(CH_3)_3$—Sn). HR-MS (ESI), (m/e): $[M+H]^+$ calculated for $[C_{37}H_{56}SnN_6O_{11}+1H]^+$, 873.3128; found at 873.3122 using the $^{112}Sn$ isotope.

(R)-(−)-5-[$^{125}$I]Iodo-3'-O-[2-(ε-(N,N0-bis(tert-butyloxycarbonyl)guanidino) hexanoyl)-2-phenylacetyl]-2'-deoxyuridine (8)

Into a glass tube containing the tin precursor 7 (100 μg, 0.1 μmol) in MeCN (50 μl), a solution of $Na^{125}I$/NaOH (10-50 μl, 44.4-373.7 MBq) was added, followed by a solution of 30% $H_2O_2$ in water (5 μl), and 2 minutes later, a solution of TFA (50 μl, 0.1% in MeCN). The resulting mixture, briefly vortexed and/or sonicated, was left for 15 minutes at room temperature and then quenched with a solution of $Na_2S_2O_3$ (90-100 μg) in water (60 μl). The reaction mixture was taken up into a syringe, and the reaction tube was washed twice with a solution of MeCN/$H_2O$ (50 μl, 1:1, v/v). The reaction mixture and washes were combined, injected onto the HPLC system, and separated on the C18 reverse phase column with a linear gradient of MeCN in water. Eluted fractions with radioiodinated product 8 were pooled, evaporated with a stream of dried nitrogen or were dissolved in dry MeCN (~18.5 MBq/ml) for further analysis or storage. This standard radioiodination of stannane 7 was carried out several times with amounts of $Na^{125}I$ ranging from 44.4 to 377.4 MBq, giving overall 482 MBq of 8. The average yield of the isolated radioactive product was 94%. A crude reaction mixture was separated and purified by HPLC on Jupiter C18 100-Å column (5 μm, 4.6×250 mm) eluted at 0.8 ml/minute using a linear gradient of MeCN in water from 50% to 60% over 20 minutes, then from 60% to 95% in 25 minutes, and 95% MeCN was held for further 15 minutes. The product was collected within 19.5-22 minutes after the injection, and an excess of the unreacted tin precursor 7, eluting ~11 minutes later, was fully separated. HPLC analysis: $t_R$=19.6 minutes (≥98% radiochemical purity, Bioscan NI(T)/UV 254 nm).

(R)-(−)-5-[$^{125}$I]Iodo-3'-O-[2-(ε-guanidinohexanoyl)-2-phenylacetyl]-2'-deoxyuridine (9)

The deprotection (HPLC monitoring) of 8 to attain 9 in a solution of 30% TFA/MeCN at room temperature required approximately 70 minutes. The treatment of 8 (dried residue, 21.8-185 MBq) with neat TFA (30 μl) at ~65° C. accelerated the elimination of the guanidine Boc protection and was completed in ~15 minutes. To remove the guanidine Boc-protective groups, neat TFA (100 μl) was added to the dried residue of 8, and the resulting mixture was vortexed and then heated in a sealed vial at 55-65° C. for 20-35 minutes. After cooling, the mixture diluted with $CH_3CN$ (200 μl) was evaporated repetitively with a stream of nitrogen, each time leaving ~20 μl of the liquid in the reaction vial to prevent the adhesion of the product to the vial's walls. This process was repeated at least three times to ensure that the excess of TFA was eliminated. The residue was then dissolved in a solution of 50% MeCN in water, injected onto the HPLC system, and was separated on ACE C18 100-Å column (5 m, 4.6×250 mm) eluted at 0.8 ml/minute with a linear gradient of MeCN from 20% to 50% over 10 minutes, then to 95% MeCN over 10 minutes, and eluting for further 15 minutes. Both solvents contained 0.07% TFA (v/v); $t_R$=11.6 minutes (≥98% radiochemical purity, Bioscan/UV 280 nm). The product eluting within 10.5-12.0 minutes after the injection was collected in three fractions, which were combined and evaporated. An average yield of the purified 9 from four preparations was 89%. Alternatively, if the initial separation of Boc-protected radioiodinated 8 was not essential, a crude radioiodination mixture of 7 was evaporated with a stream of nitrogen, and/or kept under a high vacuum, then was directly treated with neat TFA at elevated temperature, and separated using HPLC as described above. To fully eliminate the presence of TFA and $CH_3CN$, the combined HPLC fractions containing 9 were evaporated with a stream of nitrogen, and the residue ethanol (80 μl) was added followed by potassium phosphate buffer (20 μl, 10-mM PB, pH~6.1). The resulting solution was injected again onto the HPLC system equipped with Luna CN column (5μ, 4.5×250 mm) and eluted at 0.8 ml/minute with a linear gradient of 50% to 80% EtOH in 10-mM PB (pH 6.1) over a 30-minute period. The product was collected within 23.0-24.5 minutes after the injection (average $t_R$=23.4 minutes, ≥98% radiochemical purity; Bioscan). In every HPLC separation or analysis of radiolabeled products, the eluate from a column was monitored with the radioactivity detector connected to an outlet of the UV detector (detection at 220 and 280 nm). Solutions containing the product were reconstituted in a required solvent and medium at the desired concentrations and then filtered through a sterile 0.22-μm filter (MilliporeSigma, Burlington, MA) into a sterile evacuated vial. The identity of the radiolabeled product was confirmed by the evaluation of UV signals of nonradioactive iodo-analog 6 with UV and radioactivity signals of 9, $t_R$ from the radio-HPLC analyses, and by comparing $R_f$ obtained from the radio-TLC.

Stability of (R)-(−)-5-[$^{125}$I]iodo-3'-O-[2-(ε-guanidinohexanoyl)-2-phenylacetyl]-2'-deoxyuridine Aliquots of GPAID (1.4-2.3 MBq) in 120 μl of 25% EtOH/PB (10-mM, pH 6.1) were added to 6.88-ml phosphate-buffered saline (PBS), cell culture media, or serum (mouse, pig, or human). Mixtures were briefly vortexed and incubated at 37° C. and 5% $CO_2$. At selected times, 1 ml of GPAID incubation mixture was withdrawn, 1-ml MeCN was added, and the mixture was vortexed and centrifuged at 2000 rpm for 15 minutes at 4° C. The supernatant was removed, and the radioactivity measured. Supernatant (250-500 μl) were acidified to pH~6 with 0.05-N TFA (2-8 μl). The excess of MeCN was evaporated with a stream of nitrogen and 100 μl of water added. This mixture was passed through a 0.22-μm filter and 100 μl (111-185 kBq) injected onto the HPLC system. HPLC analysis of extracts proceeded on the ACE C18 100-A column (5 m, 4.6×250 mm) eluted at 0.8 ml/minute with a linear gradient of MeCN from 10% to 95% over 45 minutes and kept at 95% MeCN for 15 minutes the radioactivity detection (Bioscan). Both solvents contained 0.07% TFA (v/v).

Proteins, Sera, Buffers and Cell Culture Reagents

ATCC-formulated Eagle's Minimum Essential medium and DMEM:F-12 medium were from the American Type Culture Collection (ATCC; Manassas, VA). Fetal bovine serum (FBS) was purchased from Rockland Immunochemicals Inc. (Limerick, PA) and ThermoFisher Scientific (Waltham, MA). L-glutamine, penicillin-streptomycin and sodium pyruvate were from GE Healthcare Life Sciences (Marlborough, MA) and ThermoFisher Scientific. Pierce NE-PER™ Nuclear and Cytoplasmic Extraction Reagents and Micro BCA™ Protein Assay Kit were from ThermoFisher Scientific.

Cells

Two human NB cell lines SK-N-SH (SK) and BE(2)-C (BE) and one murine NB cell line N1E-115 (N1E) were purchased from the American Type Culture Collection (ATCC; Manassas, VA). Cells were maintained according to the vendor's instructions. For animal studies, cells were harvested when ~70% confluent and cryopreserved until ready to use.

Time- and Concentration-Dependent Cellular Uptake and Subcellular Distribution of GPAID Established protocols were used in these experiment (Kortylewicz, et al. (2020) J Med Chem., 63:2051-2073; Baranowska-Kortylewicz, et al. (1994) J Label Compd Radiopharm., 34(6):513-521; Kortylewicz, et al. (2009) J Med Chem., 52(16):5124-5143). Briefly, NB cells plated in TPP T25 flasks (Midwest Scientific, Valley Park, MO) at $5\times10^5$ cells per flask were maintained in culture for 48-72 hours, depending on the doubling time of the cell line, until 60%-70% confluent. For time-dependent uptake studies, GPAID was added to the growth medium to produce the average concentrations of 28.2±5.5, 27.6±2.8, and 30.7±1.0 kBq/ml in SK, BE, and N1E cells, respectively. Radioactive medium was removed after 1, 5, 16, 24, and 48 hours in culture (n=4 per time). Cells were harvested by scraping and enumerated using Cellometer (Nexcelom Bioscience, Lawrence, MA). Cell suspensions were centrifuged for 10 minutes at 1500 rpm; cell pellets resuspended in ice-cold PBS, transferred into microfuge tubes, and centrifuged at 500×g for 10 minutes. The radioactive content of cell pellets was measured in a gamma counter. The cellular uptake was calculated in terms of MBq per cell. For subcellular fractionation experiments, NB cells grown as monolayers were treated with GPAID and processed as described (Kortylewicz, et al. (2020) J Med Chem., 63:2051-2073). In the concentration-dependent uptake experiments, GPAID in the appropriate medium at several concentrations was added to the cell monolayers. Cells were processed after 1-hour incubation. Radioactive medium was removed, and monolayers were washed once with full nonradioactive medium and PBS. Cells were harvested and enumerated, and their radioactive content was measured.

Competition with MIBG

Cells were plated into T25 flasks and allowed to grow until ~60%-70% confluent. Fresh medium (3 ml) was added to one set of flasks (n=4 per time). To the second set of flasks (n=4 per time), fresh medium (3 ml) containing 100-μM nonradioactive MIBG was added. All cells were returned to the incubator for 30 minutes, after which time 3 ml of medium containing GPAID (51.5±1.4 kBq/ml) was added to produce the final concentration of 50-μM MIBG and 25.8±0.7 kBq/ml GPAID. Cells were returned to the incubator for additional 1, 24, and 48 hours. At designated times, media were removed, monolayer washed 1× with full medium, 2× with PBS, and SK and BE cells were harvested with the nonenzymatic cell dissociation solution (Sigma-Aldrich). N1E cells were harvested by flushing the monolayer with spent media. Cell numbers were determined, and their radioactive content measured in a gamma counter. The whole cell uptake was calculated on terms of MBq per cells. The clonogenic survival was calculated as the ratio of the number of colonies produced by cells treated with nonradioactive MIBG and GPAID to the number of colonies produced by cells treated with GPAID only. The cell survival at 24 hours was expressed as the ratio of viable cells in treatment groups to cells in untreated controls.

Mice

Research involving animals was performed in accordance with the UNMC institutional guidelines and protocols as defined by the Institutional Animal Care and Use Committee for US institutions. Athymic NCr nude mice (spontaneous mutant) were purchased from Taconic (Rensselaer, NY). The intraperitoneal route (TP) was used for the tumor implant and dose administration. All experiments were conducted in mice of both genders 4 to 8 weeks old.

Therapy

Four-week-old NCr nu/nu mice, male (n=10) and female (n=10), received IP implant of $5\times10^6$ N1E cells. One week later, mice were randomly assigned via a lottery to either control or treatment group. Control mice were given IP injection of the vehicle. Mice in the therapy group received a bolus IP injection of 3.64±0.10 MBq GPAID per mouse (~145 MBq/kg body weight [bw]). Triplicate aliquots of the injected dose (ID) were counted in a gamma counter. Syringes containing the dose and syringes after the injection were weighed on the analytical balance to determine ID. Whole body radioactivity was also measured immediately after each injection to confirm ID. Necropsy was performed at the termination of the experiment. Blood was collected via cardiac puncture. Aliquots were reserved for determination of hemoglobin (Hb; HemoCue, Ängelholm, Sweden) and hematocrit (Hct).

Statistical Analyses

All variables are expressed as average±standard deviation or ±standard error. The cellular uptake, cell survival, and other biological properties were analyzed using two-sided Student's t test. Tumor weights at necropsy were used as the final measure of response. These data were analyzed using the Mann-Whitney test. p values<0.05 were considered statistically significant. SigmaPlot/SigmaStat (Systat Software, Inc., Point Richmond, CA) and GraphPad InStat (La Jolla, CA) were used for these analyses.

Results

Synthesis of GPAID (9)

In an effort to enhance the biological half-life of IDG, a clinical candidate selected from a large series of 5-[$^{125}$I]iodo-5'-O— and -3'-O-alkanoylguanidino-2'-deoxyuridine derivatives (Kortylewicz, et al. (2020) J. Med. Chem., 63:2051-2073), the stability of its 3'-ester linkage was increased by producing sterically hindered (R)-(−)-5-[$^{125}$I]iodo-3'-O-[2-(ε-guanidinohexanoyl)-2-phenylacetyl]-2'-deoxyuridine (9, GPAID).

GPAID was prepared by inserting the (R)-(−)-2-amino-2-phenylacetyl segment at the 3'-O-position of 5-iodo-2'-deoxyuridine (IUdR). Nonradioactive (R)-(−)-5-iodo-3'-O-[2-(6-N,N'-bis(tert-butoxycarbonylguanidino)-hexanamido)-2-phenylacetyl]-2'-deoxyuridine 5 was attained as shown in FIG. 1, starting with the synthesis of (R)-methyl 2-[6-(Boc-amino)hexanamido)]-2-phenylacetate 1 through the coupling of 6-Bocaminocaproic acid with (R)-(−)-2-phenylglycine methyl ester hydrochloride with activation mediated by 2-chloro-1,3-dimethyl-2-hexafluorophosphate (CIP)/DMAP in the presence of N,N-diisopropylethylamine (DIPEA) (Kaminski, et al. (1985) Tetrahedron Lett., 26(24):2901-2904; Akaji, et al. (1994) CIP Tetrahedron Lett., 35(20):3315-3318) to give 1 in 88% yield without detectable racemization.

In subsequent steps, (R)-2-[6-(tert-butoxycarbonylamino) hexanamido]-2-phenylacetic acid 2, prepared in 91% yield by hydrolysis of the methyl ester group of 1, was reacted with the 5'-O-DMTr-20-deoxyuridine generating (R)-(−)-5-iodo-5'-O-DMTr-3'-O-[2-(6-(tert-butoxycarbonylamino)-hexanamido)-2-phenylacetyl]-2'-deoxyuridine 3 in 67% yield. The 5'-O-DMTr protecting group in 3 was cleaved with $ZrCl_4$ (Sharma, et al. (2003) J. Org. Chem., 68(11): 4574-4575). The 5'-O-deprotected 4 was isolated in 83% yield.

In the final step, the N-Boc-amino protection of 4 was removed with ~50% TFA/MeCN, and the guanidinylation of the free 6-aminohexanoyl group was achieved with N,N'-bis(tert-butoxycarbonyl)-N"-trifluoromethanesulfonyl guanidine (Baker, et al. (2002) Organic Synth., 78:91-98) to provide 5 in the overall yield of 69%. Stannane 7 was obtained with an average yield of ~39% through the stannylation of iodide 5 with hexamethylditin in the reaction catalyzed by bis-(triphenylphosphine)-palladium (II) dichloride based on the modified Stille coupling (Williams, R. (1993) Org. Synth., 71:97; Selig, et al. (2011) Tetrahedron 67(47):9204-9213), utilized to efficiently produce $^{125}$IUdR and various radioiodinated compounds (Kortylewicz, et al. (2020) J Med Chem., 63:2051-2073; Baranowska-Kortylewicz, et al. (1994) J Label Compd Radiopharm., 34(6):513-521; Kortylewicz, et al. (2009) J Med Chem., 52(16):5124-5143; Kortylewicz, et al. (2012) J Med Chem., 55(6):2649-2971; Han, et al. (2014) Prostate 74(16):1634-1646; Kortylewicz, et al. (2015) Prostate 75(1):8-22). Successive HPLC purifications were used to achieve ≥98% purity of the stannane 7. The identity of nonradioactive compounds was validated by means of $^{1}$H NMR and $^{13}$C NMR, high-resolution mass spectrometry, and meticulous HPLC analyses.

Once purified, anhydrous 7 stored with the exclusion of light under nitrogen at −20° C. was stable for several months (≤7% decomposition by HPLC). Higher hydrophobicity of stannane 7 allowed for its complete separation from the [$^{125}$I]iodinated product 8 in a single HPLC purification even if a large volume (~1 ml) of the crude reaction mixture was injected onto the column. The guanidine Boc-protective groups of 8 were removed with neat TFA at 55-65° C. GPAID 9 was isolated on HPLC. Alternatively, if the separation of Boc-protected 8 was not required, a dried crude radioiodination mixture was directly treated with neat TFA at elevated temperatures. To eliminate TFA and $CH_3CN$ from GPAID samples intended for biological studies, combined HPLC fractions containing GPAID were reinjected on HPLC and eluted with a linear gradient of EtOH in potassium phosphate buffer.

Identities of all radiolabeled products were confirmed by comparing their UV signals and $t_R$ from the radio-HPLC analysis with the UV signals of the independently prepared nonradioactive reference iodo-analogs as well as $R_f$ obtained from radio-TLC. Noncarrier-added [$^{12}$5I]iodinations conducted with 22.2 up to 148 MBq $^{125}$I always produced GPAID in high radiochemical yields of >80%-92% and radiochemical purity of ≥95%; 2% to 6% of the protodestannylated side product was detectable in some crude reaction mixtures. This by-product originated primarily from samples of stannane 7 stored at −20° C. for prolonged periods. If the radiolabeled product was stored for >18 hours, it was repurified just before use even though HPLC analyses of such samples rarely indicated the radiochemical purity<95%.

Stability Studies

Figures 2A, 2B, 2C, 2D:
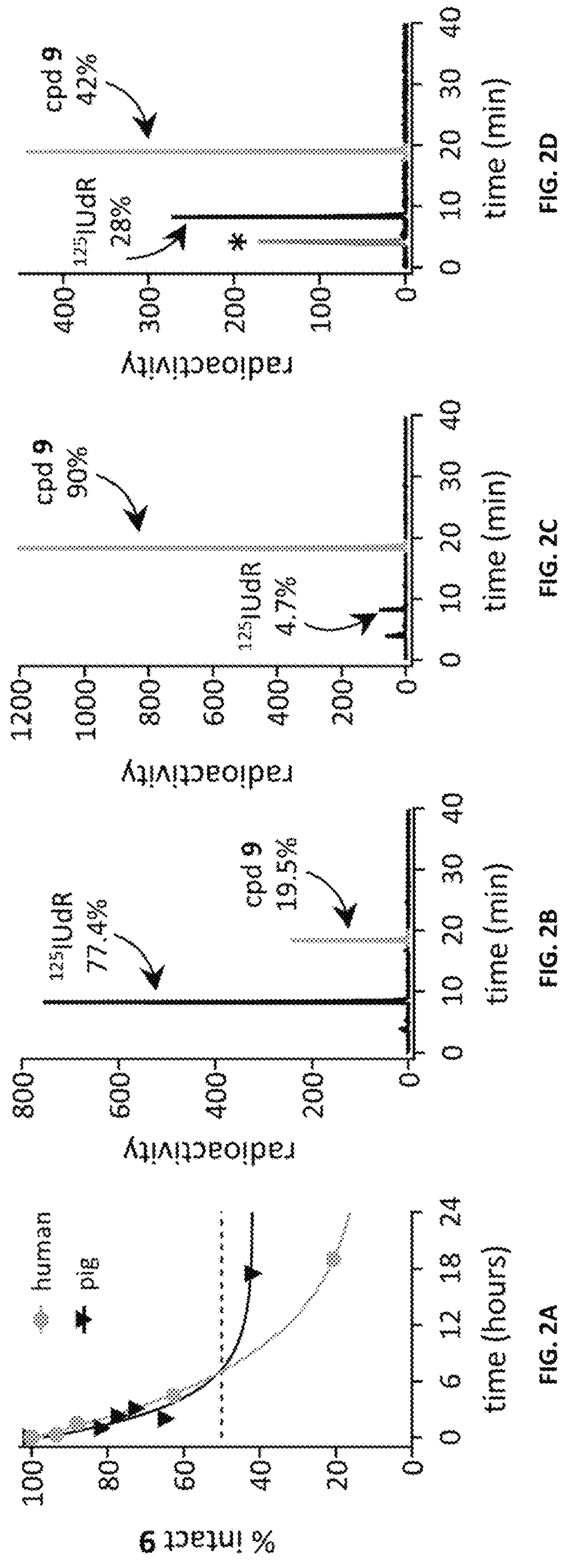
FIGS. 2A-2D show the stability of (R)-(−)-5-[$^{125}$I]iodo-3'-O-[2-(F-guanidinohexanoyl)-2-phenylacetyl]-2'-deoxyuridine (cpd 9, GPAID). High-performance liquid chromatography (HPLC) profiles of radioactive species were recovered from various incubation mixtures.

Ex vivo stability of GPAID was assessed in PBS, cell culture medium without NB cells, and in the presence of NB cells and in human, mouse, and porcine sera after various times of incubation. The analytical details are provided hereinabove. Half-lives in sera were calculated from the area under the peak of the intact GPAID recovered from the incubation mixtures plotted as a function of the incubation time. The degradation curves followed the first-order kinetics. Data were fitted into the monoexponential equations with the intercept set at 100% (FIG. 2A). In a typical experiment, a final concentration of GPAID in serum approximated radioactivity levels of $^{131}$IMIBG in blood of children receiving therapeutic doses (Pandit-Taskar, et al. (2017) Clin Nucl Med., 42(10):741-748; Matthay, et al. (1998) J Clin Oncol., 16(1):229-236). 0

Similar to IDG and other published derivatives (Kortylewicz, et al. (2020) J Med Chem., 63:2051-2073), GPAID is catabolized to $^{125}$IUdR, ensuring that the DNA cotargeting can be realized. Half-lives of GPAID in pig and human sera are 5.8±2.1 and 7.9±0.7 hours (average±SE), respectively. For comparison, the corresponding IDG half-lives were 3.6±0.1 hours and 2.3±0.1 hours (Kortylewicz, et al. (2020) J Med Chem., 63:2051-2073). The addition of the D-amino acid and a bulky phenyl group substantially increased GPAID stability in human and pig sera as compared with IDG. GPAID is not stable in mouse serum (FIG. 2D), which contains several esterases including carboxylesterase. Human and porcine sera do not contain any carboxylesterase activity (Li, et al. (2005) Biochem Pharmacol., 70(11):1673-1684; Bahar, et al. (2012) J Pharm Sci., 101(10):3979-3988).

Prior to the in vitro studies, GPAID's stability in PBS and in cell culture media was measured to confirm that the data acquired in these experiments represent properties of the intact compound. GPAID is stable in PBS and in cell culture in the absence of NB cells. FIG. 2C shows the radioactive HPLC profile of GPAID incubated in cell culture medium for 24 hours at 37° C. in 5% $CO_2$ atmosphere. After 24 hours at these conditions, >90% of GPAID remains intact. When GPAID is added to the exponentially growing monolayers of NB cell (FIG. 2D) and incubated with cells for 24 hours, the recovered media contain ~42% of the intact GPAID and ~28% of $^{125}$IUdR. Because GPAID is stable in media without cells under the identical set of conditions, the considerable loss of the intact compound and appearance of $^{125}$IUdR in the extracellular spaces are indicative of the uptake and intracellular processing. Nucleosides cross the plasma membrane of mammalian cells by a facilitated diffusion process that is bidirectional (Plagemann, et al. (1974) Biochim Biophys Acta. 344(3-4):263-305; Paterson, et al. (1981) Pharmacol Ther., 12(3):515-536). It is therefore evident that $^{125}$IUdR is produced intracellularly. If it is not taken up into DNA, $^{12}$5IUdR diffuses freely through the cellular membrane and emerges in the cell culture media.

Cellular Uptake and Subcellular Distribution of GPAID

Figures 3A, 3B, 3C:
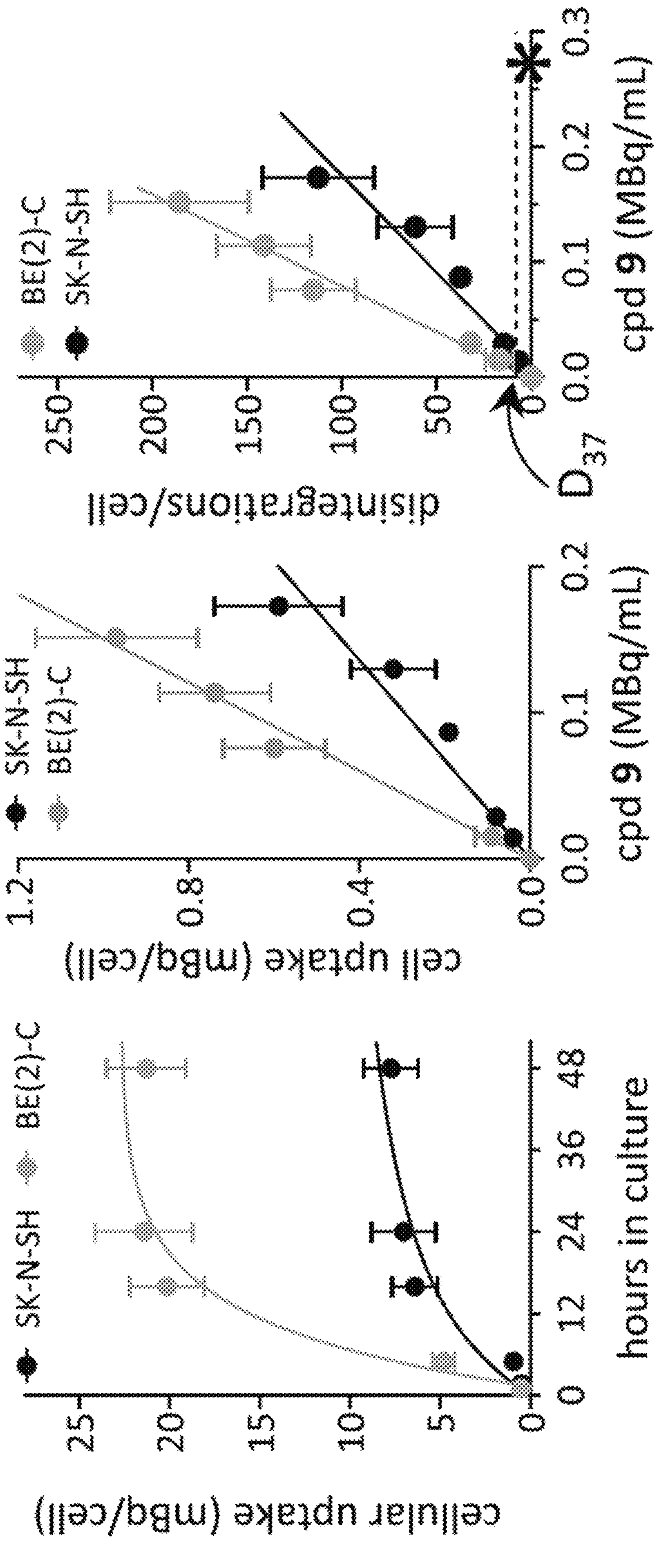
FIGS. 3A-3K provide in vitro evaluation of GPAID (cpd 9) in neuroblastoma cells.

GPAID is taken up by NB cells in a time- and concentration-dependent manner (FIG. 3A, 3B). The uptake is directly proportional to the incubation time up to 24 hours, and it is also dependent on the cell population doubling time ($T_D$). When cells are incubated with GPAID for 1 hour, washed and processed immediately, cellular uptake is nearly identical in BE cells (TD=19 hours) as it is in SK cells (TD=40 hours). However, a 5-hour incubation results in the radioactivity levels of 5.9±0.5 MBq per BE cell and 0.9±0.1 MBq per SK cell, indicating greater levels of $^{125}$I incorporation into the DNA of rapidly proliferating BE cells. At later times, the uptake per cell levels off because the number of BE cells more than doubles. Similarly to the MIBG uptake, the cellular radioactivity is directly proportional to the extracellular concentration of GPAID within the entire tested range up to 200 kBq/ml ($2.45\times10^{-9}$ M). MIBG uptake is linear up to ~$1\times10^{-7}$ M and begins to saturate at concentrations >$5\times10^{-7}$ M (Smets, et al. (1989) Cancer Res., 49(11):2941-2944). Cells incubated with different radioactive concentrations of GPAID end up with different amounts of intracellular $^{125}$IUdR. However, in this study, all cells were washed after the incubation with GPAID to remove unbound radioactivity. With this approach, as validated in the subcellular fractionation experiments, within 24 hours of GPAID treatment, virtually all $^{125}$I is incorporated into DNA. Thus, in calculating disintegrations accumulated in 24 hours (FIG. 3C), it was assumed that extranuclear $^{125}$I is low, if any, and therefore will not contribute to the radiotoxicity. NB cells accumulate >20 disintegrations per cell after a brief 1-hour exposure to GPAID at all tested concentrations >0.015 MBq/ml. $D_{37}$ for 125I in DNA of human cells is ~8.7 disintegrations per cell per 24 hours (1.3 MBq per cell per 18 hours (Kassis, et al. (1987) Radiat Res., 111(2):305-318; Makrigiorgos, et al. (1989) Radiat Res., 118(3):532-544)). Extracellular concentrations of GPAID required to achieve this level of $^{125}$I incorporation into DNA are expected to be easily attainable in a clinical setting. It is also noteworthy that all tested extracellular concentrations of GPAID are well below the clinical concentration of $^{131}$IMIBG estimated on the assumption of a uniform distribution throughout the body (denoted with an asterisk in FIG. 3C).

Figure 3E:
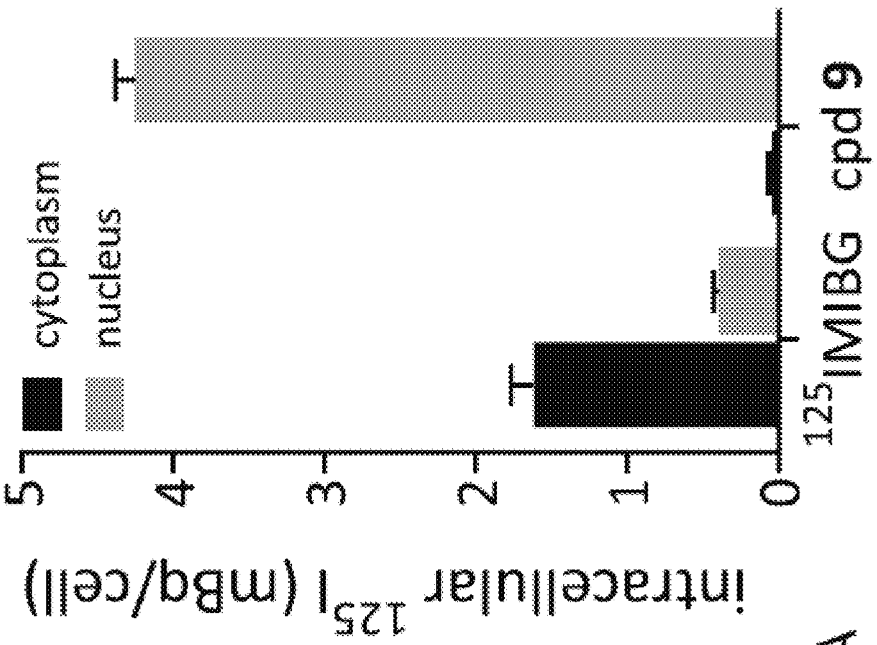
Figure 3D:
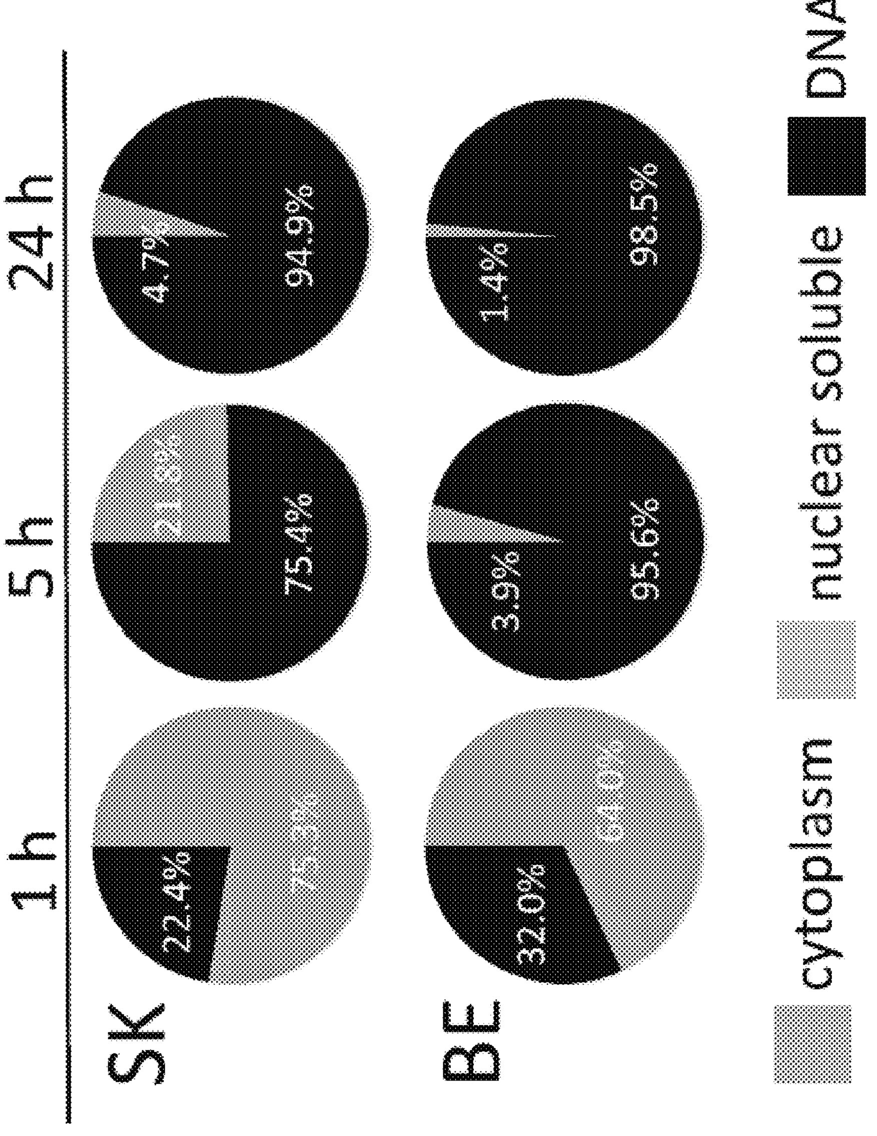

Subcellular distribution studies confirmed the intracellular processing of GPAID and production of $^{125}$IUdR as measured by the DNA-associated radioactivity (FIG. 3D). After 1 hour with GPAID, SK cells retain ~22% of the total recovered $^{125}$I in their DNA compared with 32% in DNA of BE cells. When cells are incubated for 1 hour with GPAID, washed, returned into the incubator with fresh nonradioactive medium for additional 4 hours, and then processed, nearly all cellular $^{125}$I, >95% of the total radioactivity, is associated with DNA of rapidly dividing BE cells whereas only ~75% $^{125}$ is associated with DNA of slower growing SK cells. At 24 hours, practically all $^{125}$I is associated with DNA in both cell lines. The dissimilarities in the subcellular distribution of $^{125}$IMIBG and GPAID ($T_D$=27 hours) are illustrated in FIG. 3E using N1E cells. The majority of $^{125}$IMIBG after a 24-hour incubation was recovered in the cytoplasmic fraction. Only ~19% of $^{125}$I was retrieved in the soluble nuclear fraction and 0% in DNA. In contrast, in cells exposed to GPAID, practically all $^{125}$I was recovered in the DNA pellet (>99%).

Figure 3H:
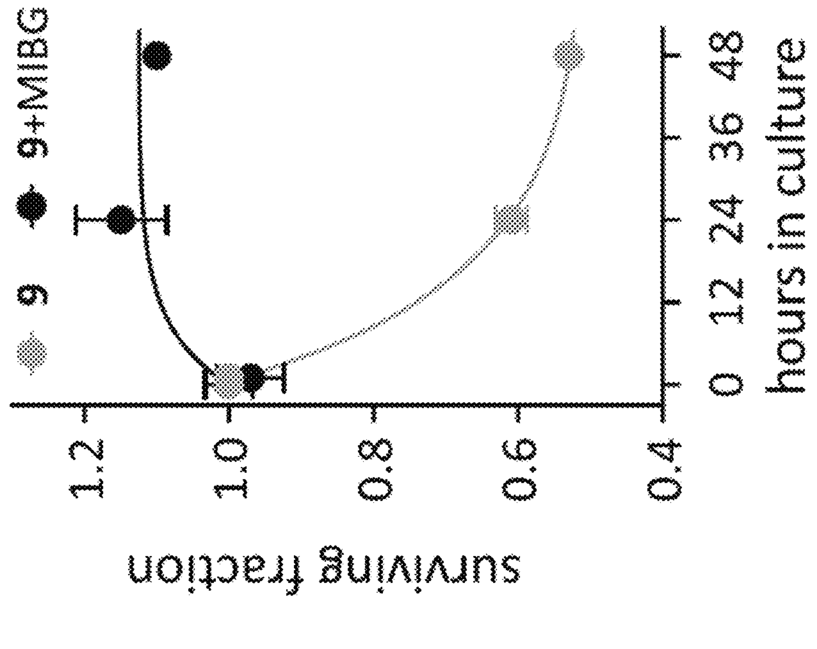
Figure 3G:
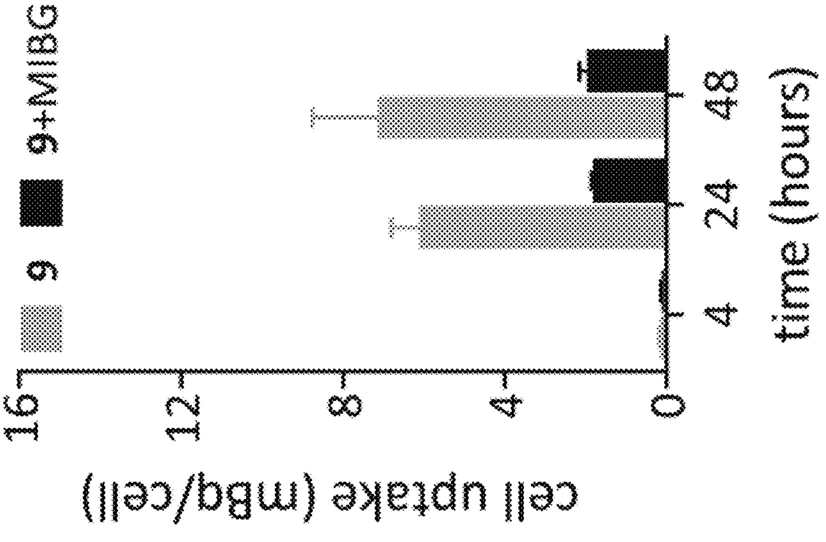
Figure 3F:
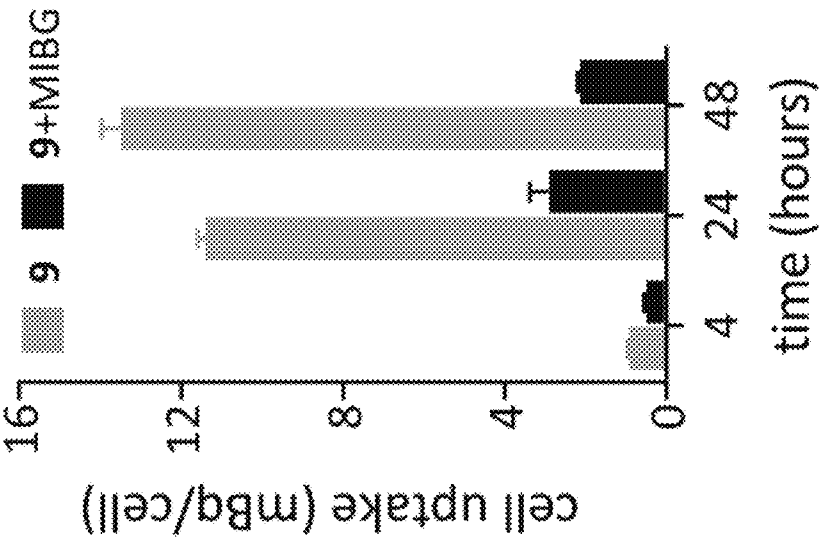
Figure 3K:
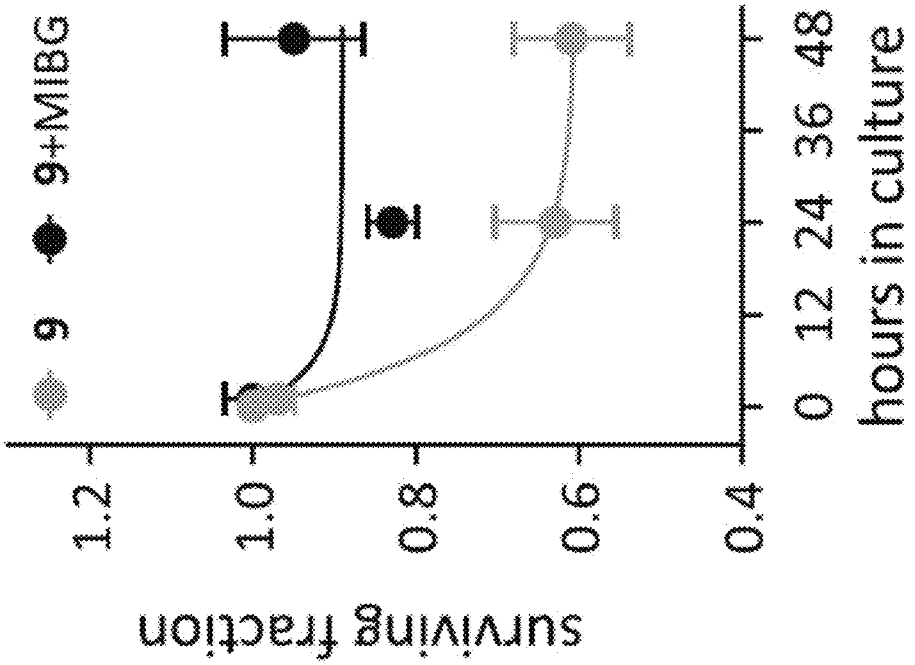
Figure 3J:
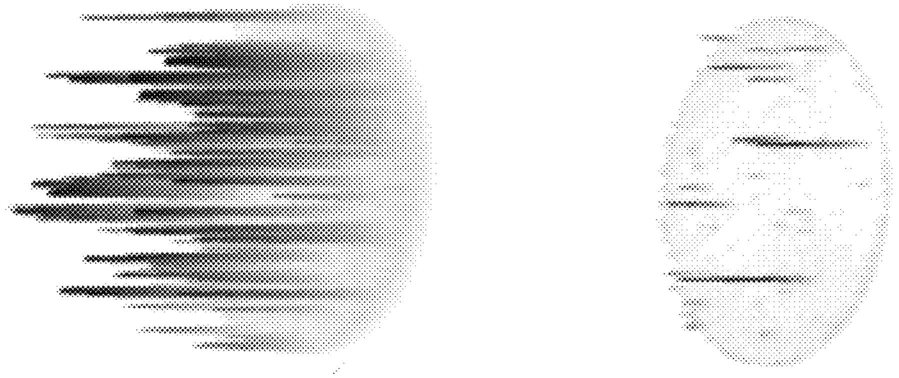
Figure 3I:
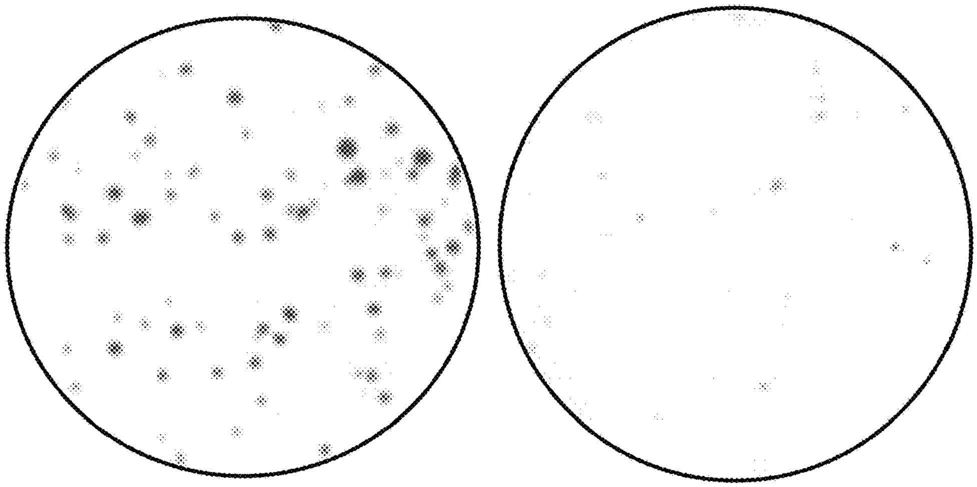

GPAID has pKa~12 and like MIBG exists at physiological pH as a monoprotonated cation, which results in a poor cell membrane permeability and hinders its cellular uptake by passive diffusion (Kortylewicz, et al. (2020) J Med Chem., 63:2051-2073; Wieland, et al. (1981) J Nucl Med., 22(1):22-31). To determine if the NET-directed uptake of GPAID is competed by MIBG, a competitive uptake assay was conducted in SK and BE cells. These cells represent a well-established robust model for the NET-specific MIBG uptake (Smets, et al. (1989) Cancer Res., 49(11):2941-2944; Montaldo, et al. (1991) Cancer Res., 51(4):4342-4346). The cell monolayer method was employed (Kortylewicz, et al. (2020) J Med Chem., 63:2051-2073). Experiments in both cell lines confirmed that the active uptake of GPAID is competitively inhibited by nonradioactive MIBG, indicating the same transport mechanism (FIG. 3F, 3G). Fifty micromolar MIBG inhibited the GPAID uptake by 70% and 85% in exponentially growing monolayers of SK and BE cells, respectively. The survival of NB cells was assessed at each time post treatment using the trypan blue exclusion method (FIG. 3H, 3K), followed by the clonogenic assay (FIG. 3I, 3J) to determine the effect of GPAID alone and when its uptake was competed with 50-μM MIBG. Both assays show significant reduction in survival when NB cells are treated with GPAID alone. As expected, the survival also depends on the duration of exposure (FIG. 3H, 3K). Cells exposed to nonradioactive MIBG alongside GPAID produced on average 3× more colonies (FIG. 3I) compared with cells treated with GPAID alone. After the treatment with GPAID at the extracellular concentration of 25.8±0.7 kBq/ml, on average, only 32% of BE cells survived, retained their reproductive integrity, and formed colonies (FIG. 3I). Colonies were considerably smaller and less intensely stained with crystal violet compared with cells treated with GPAID and MIBG. The intensity of staining is proportional to the number of cells in each colony (FIG. 3J) (Guzman, et al. (2014) PLoS ONE 9(3):e92444).

In Vivo Evaluation

Figure 4B:
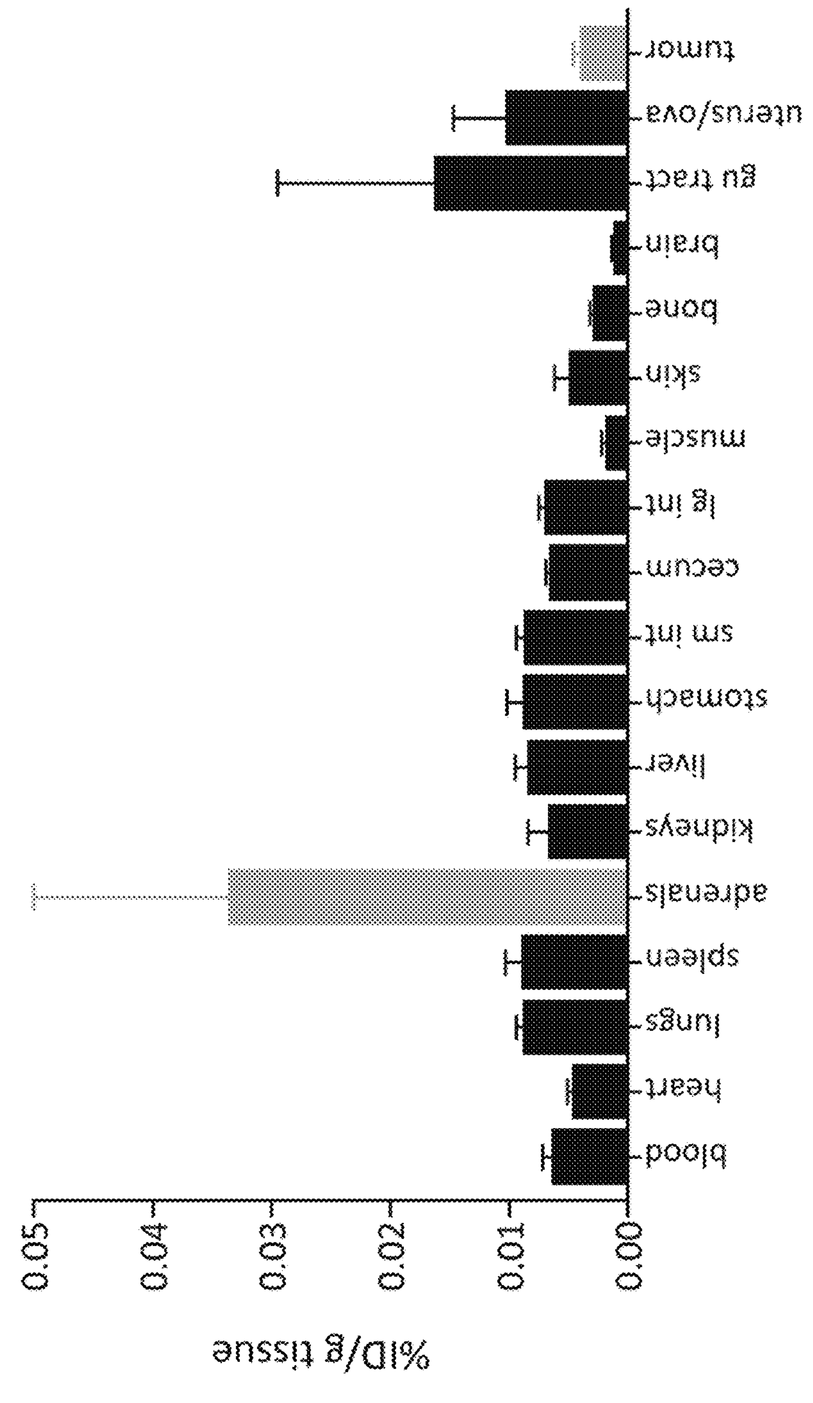
FIGS. 4A-4D shows tumor sizes, biodistribution of GPAID (cpd 9), and hemoglobin and hematocrit values in mice from the therapy and control (NT) groups.
Figure 4A:
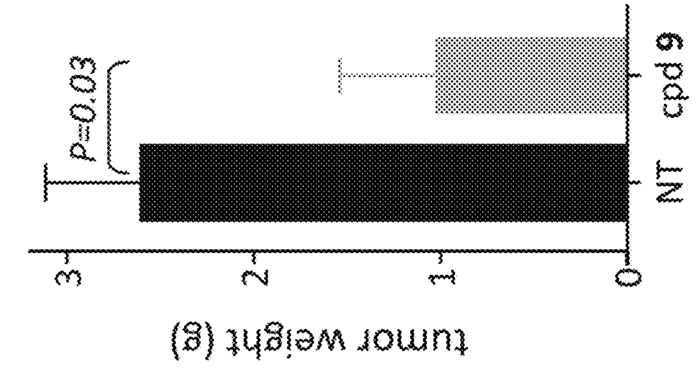
Figure 4C:
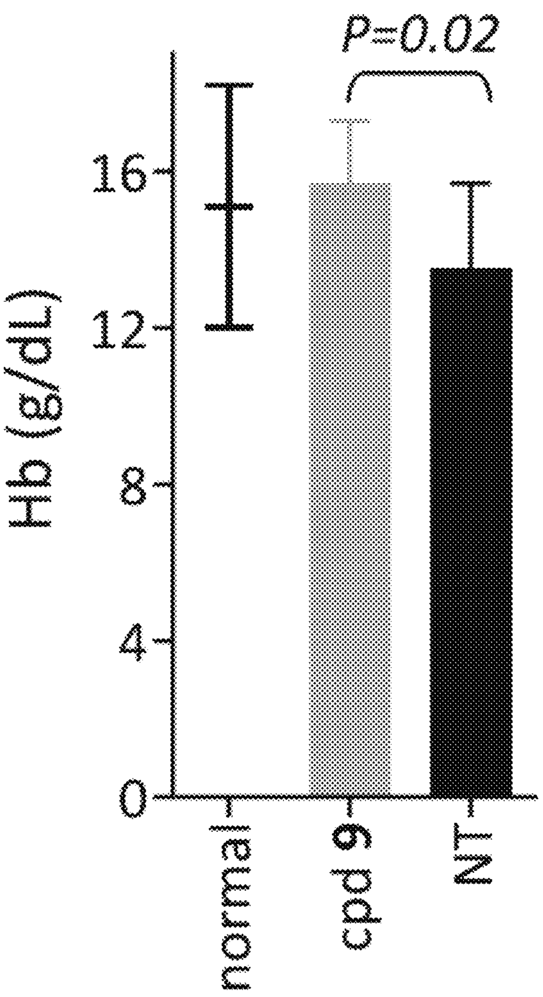
Figure 4D:
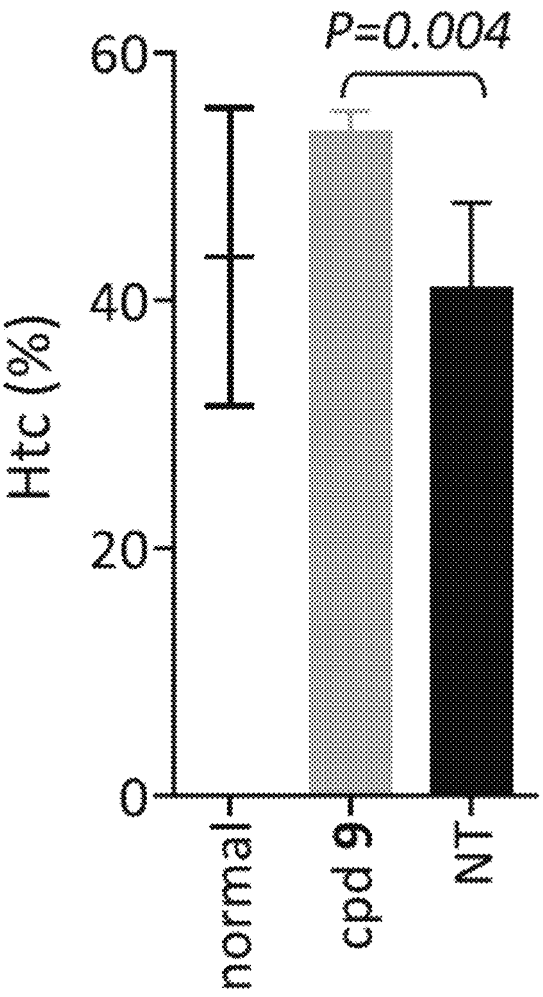

The therapeutic potential of GPAID was evaluated in mice bearing IP N1E allografts. Two factors contributed to the choice of this tumor model. First, to avoid rapid degradation of GPAID by carboxylesterases present in mouse blood (FIG. 2B), N1E cells were implanted IP, and IP injections were used as the route of GPAID administration. Second, it was determined that a mouse NB allograft represents a more realistic model of NB (Coulter, et al. (2017) J Pediatr Hematol Oncol., 39(4):272-281). Mice of both genders were treated with a single IP dose of 3.64±0.10 MBq per mouse GPAID 1 week after the tumor implant. The experiment was terminated 14 days later when control mice presented with significant abdominal distensions indicative of large tumor nodules. At necropsy, the average tumor weights were 2.61±0.57 and 0.88±0.54 g in NT and GPAID-treated mice, respectively (FIG. 4A). The difference between treatment and control groups is statistically significant (p=0.03). Hb and HCt levels in mice treated with GPAID were within the normal range values (FIG. 4C, 4D). This finding supports the postulated low toxicity of $^{125}$I-labeled compounds. Biodistribution conducted at necropsy 14 days after the dose of GPAID shows only marginal radioactivity retention in all tissues. Elevated levels of GPAID are still present in the adrenal glands 0.034±0.016% ID/g.

$^{131}$IMIBG, the first theranostic (Kimmig, et al. (1984) J Nucl Med., 25(7):773-775) introduced to the management of NB nearly 30 years ago, became an essential component of treatment strategies for relapsed and refractory disease. However, the role of $^{131}$IMIBG in NB is still debated (Gaze et al. (2013) Q J Nucl Med Mol Imaging 57(1):66-78; Wilson, et al. (2014) Eur J Cancer 50(4):801-815; Streby, et al. (2015) Pediatr Blood Cancer 62(1):5-11). Response rates, even with high-dose $^{131}$IMIBG therapy, are suboptimal. Tumor responses are only transient. High-dose therapies are associated with acute and chronic adverse effects related to the radiation exposure of normal tissues prohibiting further dose escalations (Pandit-Taskar, et al. (2017) Clin Nucl Med., 42(10):741-748). New therapies must attain a balance between improved survival rates and the morbidity of side effects. Molecular radiotherapeutics labeled with Auger-electron emitting radionuclides are expected to have more favorable toxicity profiles permitting the administration of curative doses. Here, $^{125}$I-labeled guanidine GPAID was designed to deliver radiotoxic doses of radiation to NB cell's DNA while sparing normal tissues. GPAID is a more stable analog of IDG (Kortylewicz, et al. (2020) J Med Chem., 63:2051-2073). It can be efficiently synthesized from 5-iodo-2'-deoxyuridine, a molecular radiotherapy platform with clinically proven minimal toxicities and DNA-targeting properties. Incorporation of an unnatural amino acid residue into the structure of radioactive guanidine increases stability. GPAID undergoes intracellular processing, and its catabolite $^{125}$IUdR is incorporated into DNA of NB cells with high proliferation activities, that is, cells in the high-risk and aggressive disease. Tumor responses to clinically manageable doses of GPAID are significant in mouse allografts of NB. The chemical structure accommodates therapeutic as well as diagnostic radionuclides. Biological properties of GPAID indicate its significant potential as a novel theranostic for the management of NB.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound of Formula (I):

(I)

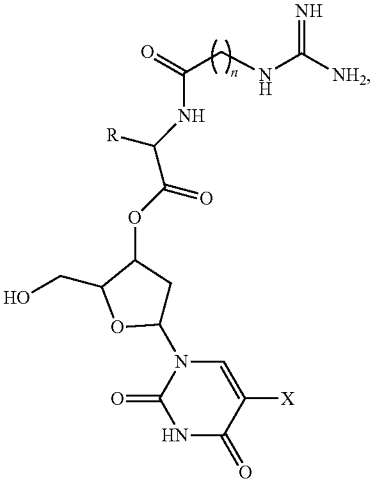

wherein X is a radionuclide or a chelating agent comprising a radionuclide; wherein said chelating agent is optionally attached via a linker; wherein R is an optionally substituted aryl or heteroaryl; and wherein n=1-5, or a pharmaceutically acceptable salt or stereoisomer thereof.

2. The compound of claim 1, wherein the compound is of Formula (II):

(II)

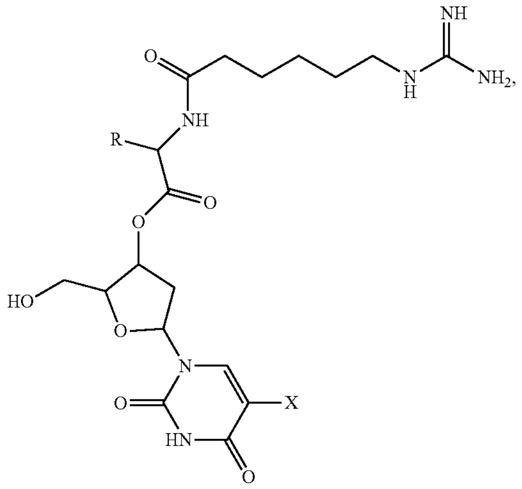

or a pharmaceutically acceptable salt or stereoisomer thereof.

3. The compound of claim 1, wherein the compound is of Formula (III):

(III)

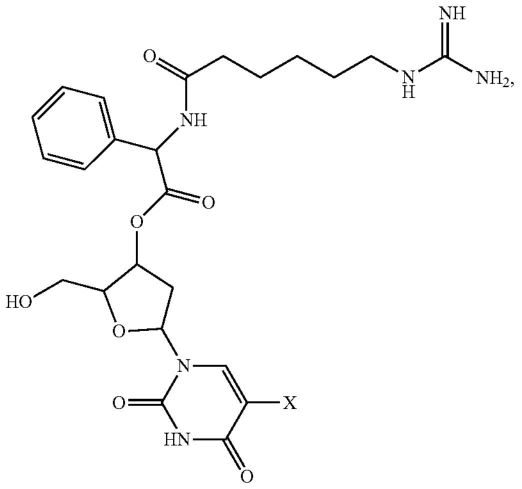

or a pharmaceutically acceptable salt or stereoisomer thereof.

4. The compound of claim 1, wherein X is an Auger electron-emitting radionuclide.

5. The compound of claim 1, wherein X is a radiohalogen.

6. The compound of claim 1, wherein X is selected from the group consisting of $^{123}$I, $^{124}$I, $^{125}$I, $^{131}$I, $^{211}$At, $^{18}$F, $^{76}$Br, $^{77}$Br, and $^{80m}$Br.

7. The compound of claim 1, wherein X is a radioactive iodine.

8. The compound of claim 1, wherein X is selected from the group consisting of $^{123}$I, $^{124}$I, and $^{125}$I.

9. The compound of claim 1, wherein X is a radionuclide.

10. The compound of claim 1, wherein R is aryl.

11. The compound of claim 1, wherein the aryl or heteroaryl is substituted by at least one $C_1$-$C_3$ alkyl, $C_2$-$C_4$ alkenyl, $C_1$-$C_3$ alkoxy, $C_1$-$C_3$ monoalkylamino, $C_1$-$C_3$ dialkylamino, halogen, —OH, —SH, —$NH_2$, —COOH, —CN, and/or —$NO_2$.

12. A composition comprising a compound of claim 1 and a pharmaceutically acceptable carrier.

13. A method of treating, inhibiting, and/or preventing a cancer or other norepinephrine transporter associated disease or disorder in a subject in need thereof, said method comprising administering a compound of claim 1 to the subject.

14. The method of claim 13, said method further comprising administering another therapy to said subject.

15. The method of claim 13, wherein said cancer is neuroblastoma.

16. A method for imaging and/or detecting cancer or other norepinephrine transporter associated disease or disorder in a subject, said method comprising:

a) administering a compound of claim 1 to the subject; and b) detecting the presence of the radioactivity from said radionuclide from said subject, wherein the presence and/or location of the radioactivity provides for the detection and/or image of the cancer or other norepinephrine transporter associated disease or disorder in said subject.

17. The method of claim 16, wherein the radionuclide is a gamma emitting isotope and step b) comprises performing a single photon emission computed tomography (SPECT) or scintigraphy.

18. The method of claim 16, wherein the radionuclide is a positron emitting isotope and step b) comprises performing a positron emitting tomography (PET).

19. A method for monitoring the progression of a cancer or other norepinephrine transporter associated disease or disorder in a subject, said method comprising:

a) administering a compound of claim 1 to the subject; and b) detecting the presence of the radioactivity from said radionuclide in said subject, wherein the presence and/or location of the radioactivity provides for the detection and/or image of the cancer or other norepinephrine transporter associated disease or disorder in said subject; and wherein step b) or step a) and step b) are performed at different timepoints on the subject.

20. The method of claim 19, wherein said cancer is neuroblastoma.

21. The composition of claim 12, further comprising an anti-cancer therapeutic agent.

* * * * *